United States Patent [19]

Wilkerson

[11] Patent Number: 5,039,706

[45] Date of Patent: Aug. 13, 1991

[54] ANTIINFLAMMATORY PLA$_2$ INHIBITORS

[75] Inventor: Wendell W. Wilkerson, New Castle, Del.

[73] Assignee: Du Pont Merck Pharmaceutical Company, Wilmington, Del.

[21] Appl. No.: 386,925

[22] Filed: Jul. 28, 1989

Related U.S. Application Data

[63] Continuation-in-part of Ser. No. 126,616, Nov. 30, 1987, abandoned.

[51] Int. Cl.$^5$ .................. A61K 31/135; C07C 211/00
[52] U.S. Cl. .................................... 514/649; 514/654; 564/367
[58] Field of Search ................. 564/367; 514/649, 654

[56] References Cited

U.S. PATENT DOCUMENTS 3,979,444  9/1976  Ledniger ........................... 260/490
4,239,780  12/1980  Wallach ............................. 424/330

FOREIGN PATENT DOCUMENTS 713536  6/1971  South Africa .

OTHER PUBLICATIONS

Wallach et al., Biochemical Pharmacology, 30, 1315 (1981).

*Primary Examiner*—Leonard Schenkman

[57] ABSTRACT

The invention relates to benzylamine phosphilipase A$_2$ inhibitors, pharmaceutical compositions containing them, and methods of treating phospholipase A$_2$-mediated conditions in mammals by administration of a therapeutically effective amount of such a benzylamine phospholipase A$_2$ inhibitor.

51 Claims, No Drawings

ANTIINFLAMMATORY PLA₂ INHIBITORS

This is a continuation-in-part of application Ser. No. 07/126,616 filed Nov. 30, 1987, now abandoned.

BACKGROUND OF THE INVENTION

This invention relates to benzylamines and processes for their preparation, pharmaceutical compositions containing them and pharmaceutical methods using them. These compounds have shown activity as inhibitors of the enzyme phospholipase $A_2$.

The important role of phospholipase $A_2$ in the biosynthesis of prostaglandins and leukotrienes indicates that inhibitors of phospholipase $A_2$ may be valuable therapeutic agents having wide applicability in inflammatory and/or allergic conditions in mammals. Although some currently-available anti-inflammatory agents show activity against phospholipase $A_2$ or other enzymes of the "arachidonic acid cascade", there is a continuing need for safer and more effective drugs capable of treating inflammatory and/or allergic diseases.

U.S. Pat. No. 4,239,780 (issued to D. P. Wallach on Dec. 16, 1980) discloses the use for treating phospholipase $A_2$ mediated conditions of compounds of the formula:

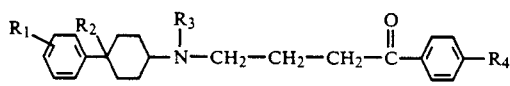

wherein
- $R_1$ is 4-Cl, 4-CF₃, H, or 2- or 4-CH₃;
- $R_2$ is CH₃—O—, —CH₂—OH, or H;
- $R_3$ is H or CH₃; and
- $R_4$ is F or Cl.

These compounds and their activities as inhibitors of phospholipase $A_2$ are also described in D. P. Wallach and V. J. R. Brown, *Biochemical Pharmacology*, 30, 1315 (1981).

SUMMARY OF THE INVENTION

It has been found that compounds of Formula I are phospholipase $A_2$ (PLA₂) inhibitors and are useful in treating inflammation in mammals.

$$R—X—(CH_2)_n—\underset{NH_2}{CH}—Ar \quad\quad I$$

where
Ar is

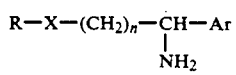

and Z is H, F, Cl, Br, OR¹, or S(O)ₘR¹ where R¹ is H, methyl, or ethyl, and m is 0, 1, or 2;
n is 1 to 5;
X is NH, S(O)ₚ, or O; p is 0, 1, or 2; and
R is $C_{7-20}$ alkyl, pyridyl, or a mono- or polycyclic benzoid aromatic system of the formula:

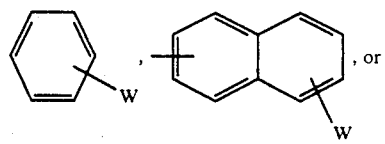

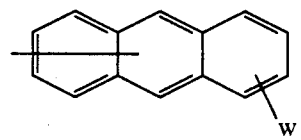

where W is $C_{1-20}$ alkyl, F, Cl, Br, —OR², —S(O)_qR², —C(CF₃)₂OH, or phenyl, and R² is methyl or ethyl, and q is 0, 1, or 2; or R is benzhydryl, phenyl-(4-pyridyl)methyl, alkaryl or substituted alkaryl of 7 to 25 carbon atoms where the substitution is on the aromatic moiety, and is F, Cl, Br, OR³, S(O)ᵣR³, or $C_{1-10}$ alkyl, where R³ is methyl or ethyl, and r is 0, 1, or 2;

provided that
- a. when Z is H, X is NH, and n is 2, then R cannot be benzhydryl;
- b. when X is NH, then R cannot be phenyl or benzyl;
- c. when X is S, W cannot be OCH₃; and
- d. when X is O, n cannot be 2.

Preferred, for reasons of high activity and/or ease of synthesis are compounds of Formula I described above and their pharmaceutically acceptable salts
wherein
Ar is

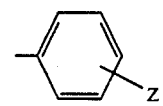

and Z is H, F, Cl, Br, —OCH₃, or S(O)ₘCH₃, where m is 0, 1, or 2;
n is 1, 2, or 3;
X is NH or S.

More preferred are the compounds of Formula I described above and their pharmaceutically acceptable salts
wherein
Ar is

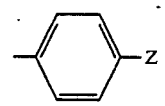

where Z is H, F, Cl, OCH₃, or SCH₃;
n is 2 or 3;
X is NH or S; and
R is $C_{10-12}$ alkyl, or

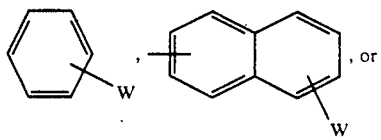

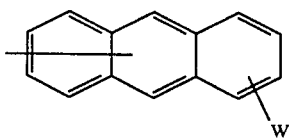

where W is $C_{1-12}$ alkyl;

or R is alkaryl or substituted alkaryl of 7 to 25 carbon atoms, where the substitution is on the aryl moiety and is $OCH_3$, $SCH_3$, F, Cl, or $C_{1-10}$ alkyl.

Specifically preferred compounds of the invention are:

| EX. NO. | |
|---|---|
| 1 | α-(2-[1,4a-Dimethyl-7-(2-propyl)-1,2,3,4,4a,9,10,10a-octahydro-1-phenanthrenylmethylamino]ethyl)-4-fluoro-benzenemethanamine Dihydrochloride. |
| 2 | 4-Fluoro-α-[3-(3-methylphenylthio)propyl]benzenemethanamine Hydrochloride. |
| 6 | 4-Fluoro-α-(2-[2-(2-naphthalenyl)ethylamino]ethyl)benzenemethanamine Dihydrochloride. |
| 8 | 4-Fluoro-α-(4-[1,4a-dimethyl-7-(2-propyl)-1,2,3,4,4a,9,10,10a-octahydro-1-phenanthrenylmethylamino]propyl)benzenemethanamine Dihydrochloride. |
| 18 | 4-Fluoro-α-(3-[(2-naphthalenyl)ethylamino]propyl)benzenemethanamine Dihydrochloride. |
| 24 | 4-Fluoro-α-[3-(4-methylphenylthio)propyl]benzenemethanamine. |
| 32 | 4-Methylthio-α-(2-[2-(2-naphthalenyl)ethylamino]ethyl)benzenemethanamine Dihydrochloride. |
| 35 | 4-Fluoro-α-(2-decylaminoethyl)benzenemethanamine Dihydrochloride. |
| 50 | 4-Methoxy-α-(2-[2-(2-naphthalenyl)ethylamino]ethyl)benzenemethanamine Dihydrochloride. |
| 56 | 2-(2-[1,4a-Dimethyl-7-(2-propyl)-1,2,3,4,4a,9,10,10a-octahydro-1-phenanthrenylmethylamino]ethyl) benzenemethanamine Dihydrochloride. |
| 57 | α-(2-[1,4a-Dimethyl-7-(2-propyl)-1,2,3,4,4a,9,10,10a-octahydro-1-phenanthrenylmethylamino]ethyl)-4-methoxy-benzenemethanamine Dihydrochloride. |
| 58 | α-(2-[1,4a-Dimethyl-7-(2-propyl)-1,2,3,4,4a,9,10,10a-octahydro-1-phenanthrenylmethylamino]ethyl)-4-methylthio-benzenemethanamine Dihydrochloride. |

DETAILED DESCRIPTION OF THE INVENTION

The compounds of this invention have demonstrated pharmacological activity as inhibitors of the enzyme phospholipase $A_2$ ($PLA_2$). Phospholipase $A_2$ acts to release arachidonic acid from phospholipids. Once released, arachidonic acid is rapidly metabolized by a variety of enzymes of the "arachidonic acid cascade." The products of the arachidonic acid cascade include prostaglandins, leukotrienes, and related compounds. These compounds exhibit a remarkably broad spectrum of biological activity, and inhibition of their biosynthesis is recognized as a valuable mechanism for production of anti-inflammatory effects.

Both prostaglandins and leukotrienes are believed to have important functions as mediators of inflammation and currently available drugs which inhibit their production are of significant therapeutic value in man and other mammals. Nonsteroidal anti-inflammatory agents such as the salicylates act as inhibitors of prostaglandin synthesis from arachidonic acid by inhibiting the cyclooxygenases. This inhibition of prostaglandin synthesis is believed to be the basis for many of the therapeutic effects of the aspirin-like drugs. The anti-inflammatory activity of the glucocorticosteroids, on the other hand, is believed to be at least partly due to their ability to induce the biosynthesis of a phospholipase $A_2$ inhibitor protein, thereby diminishing the release of arachidonic acid from phospholipids. By decreasing concentrations of arachidonic acid, the substrate for the entire arachidonic acid cascade, production of leukotrienes as well as prostaglandins can be decreased.

Many diseases and conditions in man and other mammals have inflammatory and/or allergic components believed to be mediated by phospholipase $A_2$, e.g., rheumatoid arthritis and other rheumatic disorders, various collagen diseases, dermatoses, psoriasis, hypersensitivity and immune reactions, bronchospastic diseases such as asthma, and disorders of platelet aggregation. Because the compounds of this invention have shown activity as $PLA_2$ inhibitors, valuable pharmacological activity in these and other diseases or conditions mediated by the various products of the arachidonic acid cascade is to be expected.

SYNTHESIS

The compounds of this invention can be illustrated by Formula I, which can be isolated as the free base or as pharmaceutically acceptable salts of such acids (HA) as hydrochloric acid, hydrobromic acid, sulfuric acid, phosphoric acid, acetic acid, formic acid, citric acid, maleic acid, p-toluenesulfonic acid, or tartaric acid. These compounds can be prepared according to Eq. 1a by the reduction

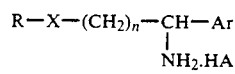

of an oxime or methoxime (II, where R is hydrogen or methyl) derivative with borane-tetrahydrofuran complex ($BH_3 \cdot THF$), lithium aluminum hydride (LAH), or catalytic hydrogenation in a solvent such as diethyl ether ($Et_2O$), tetrahydrofuran (THF), dimethoxyethane (DME), or dioxane, at a temperature between 0° C. and the solvent reflux temperature.

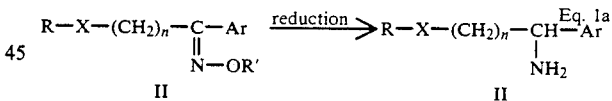

Alternatively, the compounds of this invention can be prepared by the use of the Leuckart Reaction (M. L. Moore, Org. Reactions, 5(7), 301 (1949)). This procedure involves the reductive amination of a ketone as illustrated in Equation 1b.

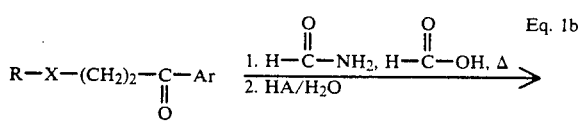

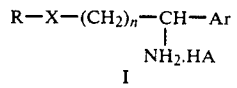

An alternative to this approach involves the reductive amination of a ketone (III) with ammonium acetate and sodium cyanoborohydride in the presence of an acid such as acetic acid, as illustrated in Equation 1c.

$$R-X-(CH_2)_n-\underset{\underset{O}{\|}}{C}-Ar \xrightarrow[HOAc]{NH_4OAc, NaCNBH_3} \quad \text{Eq. 1c}$$

III $$R-X-(CH_2)_n-\underset{\underset{NH_2}{|}}{CH}-Ar$$

I

The ketone (III) can also be converted to the oxime (II) used in Eq. 1a by reactions with hydroxylamine or methoxyamine in the presence of a base such as potassium carbonate, sodium hydroxide, potassium hydroxide, or pyridine in a solvent such as ethanol. The reaction can be conducted as illustrated in Equation 2 at a temperature between 25° C. and the solvent reflux temperature.

$$R-X-(CH_2)_n-\underset{\underset{O}{\|}}{C}-Ar \xrightarrow[solvent]{H_2N-OR', base} \quad \text{Eq. 2}$$

III $$R-X-(CH_2)_n-\underset{\underset{N-OR'}{\|}}{C}-Ar$$

II

The ketones (III) used in this invention can be prepared by alkylating an amine (X=N), thiol (X=S), or alcohol (X=O) with a haloalkyl-phenone or its ketal, or an α,β-unsaturated ketone as shown in Equation 3.

a. $R-X-H + Halo-(CH_2)_n-\underset{\underset{O}{\|}}{C}-Ar$     Eq. 3 b. $R-X-H + CH_2=CH-\underset{\underset{O}{\|}}{C}-Ar \quad\to\quad R-X-(CH_2)_n-\underset{\underset{O}{\|}}{C}-Ar$

III c. $R-X-H \xrightarrow[2.\ HA/H_2O]{1.\ Halo-(CH_2)_n-\underset{\underset{OR''}{|}}{\overset{\overset{OR''}{|}}{C}}-Ar}$ Alternatively, when n=2, the ketone (III) can be prepared by employing the Mannich Reaction (F. F. Blicke, *Org. Reactions*, 1(10), 303 (1942)), which involves the reaction of an amine hydrochloride, formaldehyde, and an acetophenone to give a β-aminoketone as illustrated in Equation 4.

$$R-NH_2 \cdot HCl + H-\underset{\underset{O}{\|}}{C}-H + CH_3-\underset{\underset{O}{\|}}{C}-Ar \xrightarrow[\Delta]{EtOH} \quad \text{Eq. 4}$$

$$R-NH-(CH_2)_2-\underset{\underset{O}{\|}}{C}-Ar$$

Compounds of Formula I where n is 3 and X is NH can be prepared by reacting a substituted 3-benzoylpropionic acid halide with a primary amine, or by reacting the acid component with ethyl or tert-butyl chloroformate to form the mixed anhydride which is then allowed to react with the amine. Other coupling agents, such as dicyclohexylcarbodiimide, can be used to activate the carboxyl moiety to form the ketoamide. The resulting ketoamide can be reacted with hydroxylamine or methoxyamine to give the corresponding oxime. The oxime-amide can be chemically reduced with lithium aluminium hydride or borane reagents to give the desired diamine.

$$Ar-\underset{\underset{O}{\|}}{C}-CH_2-CH_2-\underset{\underset{O}{\|}}{C}-OH \xrightarrow[base]{Cl-\underset{\underset{O}{\|}}{C}-OEt}$$

$$[Ar-\underset{\underset{O}{\|}}{C}-CH_2-CH_2-\underset{\underset{O}{\|}}{C}-O-\underset{\underset{O}{\|}}{C}-OEt] \xrightarrow{R-NH_2}$$

$$R-NH-\underset{\underset{O}{\|}}{C}-CH_2-CH_2-\underset{\underset{O}{\|}}{C}-Ar \xrightarrow[base]{MeO-NH_2}$$

$$R-NH-\underset{\underset{O}{\|}}{C}-CH_2-CH_2-\underset{\underset{N-OMe}{|}}{C}-Ar \xrightarrow[2.\ HCl/H_2O]{1.\ BH_3 \cdot THF,\ \Delta}$$

$$R-NH-CH_2-CH_2-CH_2-\underset{\underset{NH_2}{|}}{CH}-Ar$$
$$2HCl$$

Compounds of Formula I may exist as racemic, diastereomeric mixtures, or their optically pure isomers.

The compounds of the invention and their synthesis are further illustrated by the following examples. All temperatures are in degrees Celsius. Solvent ratios for thin-layer chromatography (tlc) are by volume.

EXAMPLE 1

α-(2-[1,4a-Dimethyl-7-(2-propyl)-1,2,3,4,4a,9,10,10a-octahydro-1-phenanthrenylmethylamino]ethyl)-4-fluorobenzenemethanamine Dihydrochloride A.
1-(4-Fluorophenyl)-3-([1,4a-dimethyl-7-(2-propyl)1,2,3,4,4a,9,10,10a-octahydro-1-phenanthren-1-yl]methylamino)-1-propanone 4-Methylbenzene Sulfonic Acid Salt A solution of 3-chloro-4'-fluoropropiophenone (37.3 g, 0.2 mole) in tetrahydrofuran (100 ml) was treated with triethylamine (22.3 g, 0.22 mole) and stirred at room temperature for one hour. The triethylamine hydrochloride was removed by filtration, and the filtrate was added to a mixture of dehydroabietylamine (57.1 g, 0.2 mole) and p-toluenesulfonic acid monohydrate in tetrahydrofuran (100 ml). The mixture was heated at reflux for 20 hours and concentrated in vacuo. The residue was triturated with water (400 ml) to give a yellow gum. The aqueous phase was decanted, and the crude product was triturated with diethyl ether (200 ml). The resulting white crystals were collected by filtration, washed with more diethyl ether, and dried to yield the title compound (58.0 g, 48%); mp 157°-158° C.; IR(nujol) C=O @ 1685 cm$^{-1}$; NMR(DMSO-d$_6$, TMS): δ0.6-2.0(m,24H), 2.27(s,3H,ArCH₃), 2.77(m,1H), 2.87(m,2H,CH₂—CO), 3.10(m,1H), 3.50 and 3.73(2m,4H,CH₂—N—CH₂), 6.87-8.0(m,11-H,aromatic); Anal. Calcd. for C₂₉H₃₈ FNO.C₇H₈O₃S, MW 607.82: C,71.13; H,7.63; N,2.31; S,5.28. Found: C,71.10; H,7.86; N,2.46; S,5.46. Mass spectrum m/e 435; [α]$_D^{25}$ 15.8° (c,1.01,MeOH).

B.

1-(4-Fluorophenyl)-3-([1,4a-dimethyl-7-(2-propyl)-1,2,3,4,4a,9,10,10a-octahydro-1-phenanthren-1-yl]methylamino)-1-propanone o-methyloxime hydrochloride A mixture of the ketone from part A (30.4 g, 0.05 mole) and methoxylamine hydrochloride (8.4 g, 0.1 mole) in a mixture of pyridine-ethanol (1:1,150 ml) was stirred at room temperature for 72 hours and concentrated in vacuo. The residue was cooled in an ice bath and triturated with cold water (400 ml). The resulting solid was collected by filtration, washed with cold water and diethyl ether, and dried to yield the title compound (22.0 g,88%); mp 185°-187° C.; IR(nujol): no carbonyl; NMR(DMSO-d₆, TMS): δ3.77 and 3.97(2s,3H,OCH3, 15:85), 6.7-7.2(m,3H,trisubstituted phenyl), 7.87(m,4H, p-F-phenyl); Anal. Calcd. for C₃₀H₄₁FN₂O.HCl, MW 501.13: C,71.90; H,8.45; N,6.59. Found: C,72.15; H,8.13; N,5.35. Mass spectrum m/e 464,209; [α]$_D^{25}$+21.3° (c,0.98,MeOH).

C.

α-(2-[1,4a-Dimethyl-7-(2-propyl)-1,2,3,4,4a,9,10,10a-octahydro-1-phenanthrenylmethylamino]ethyl)-4-fluorobenzenemethanamine Dihydrochloride The methyl oxime from part B (14.8 g, 0.03 mole) was suspended in dry tetrahydrofuran (50 ml), cooled in an ice bath, treated with borane-tetrahydrofuran complex (1M, 90 ml, 0.09 mole), stirred at room temperature for 16 hours, and heated at reflux for six hours. The excess borane was decomposed with cold water, and the mixture was concentrated in vacuo. The residue was treated twice with methanol (100 ml) and evaporated. The residue was digested with hydrochloric acid (6N, 100 ml) at 80° C. for one hour and concentrated in vacuo. The residue was partitioned between methylene chloride (200 ml) and sodium hydroxide (1N, 200 ml). The organic phase was washed with water and brine, dried over anhydrous magnesium sulfate, filtered, and concentrated to a volume of 25 ml. The solution was treated with hydrogen chloride-diethyl ether (1N) until no further precipitation was observed. The resulting solid was collected by filtration, washed with diethyl ether, and dried to yield the title compound (13.7 g, 91%), mp 215° C. dec.; NMR(DMSO-d₆, TMS): δ4.43(m,1H,N—C—H),
[6.83(s,1H)+6.93(d,1H)+7.13(d,1H) trisubstituted phenyl], [7.30(d of d,2H) and 7.70(m,2H) p-F-phenyl]; Anal. Calcd. for C₂₉H₄₁FN₂.2HCl, MW 509.56: C,68.35; H,8.50; N,5.50. Found: C,68.77; H,8.57; N,5.37. Mass spectrum m/e 436,181. [α]$_D^{25}$+10.3(c,1.05,MeOH).

EXAMPLE 2

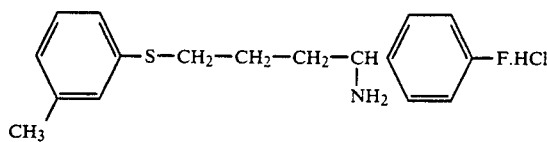

4-Fluoro-α-[3-(3-methylphenylthio)propyl]benzenemethanamine Hydrochloride

A.

1-(4-Fluorophenyl)-4-(3-methylphenylthio)-1-butanone

A solution of 3-thiocresol (25.0 g, 0.2 mole) and 4-chloro-4'-fluorobutyrophenone (40.1 g, 0.2 mole) in tetrahydrofuran (200 ml) was treated with triethylamine (22.3 g, 0.22 mole) and refluxed for six hours under nitrogen. The mixture was concentrated in vacuo, and the residue was partitioned between diethyl ether (200 ml) and water (200 ml). The organic layer was washed three times with sodium hydroxide (1N), water, and brine; dried over anhydrous magnesium sulfate, filtered, and concentrated to a pure oil by tlc (n-butyl chloride) to yield the title compound (57.0 g, 99%); IR(nujol): C=O @ 1686 cm⁻¹; NMR(CDCl₃, TMS): δ2.08(m,2H,CH₂), 2.30(s,3H,ArCH₃), 3.00(t,2H,CH₂—CO), 3.10(t,2H,S—CH₂), 6.9-7.17(m,4H, 1,3-substituted phenyl), [7.10(d of d, 2H) and 7.97(m,2H) p-F-phenyl]; Anal. Calcd. for C₁₇H₁₇FNOS, MW 288.38: C,70.80; H,7.97; S,11.12. Found: C,70.79; H,6.01; S,11.18. Mass spectrum m/e 288,150.

B.

1-(4-Fluorophenyl)-4-(3-methylphenylthio)-1-butanone-O-methyloxime

A solution of the ketone from part A (25.0 g, 0.087 mole) in pyridine-ethanol (1:1, 150 ml) was treated with methoxylamine hydrochloride (14.5 g, 0.17 mole) and heated at reflux for 24 hours. The mixture was concentrated in vacuo, and the residue was partitioned between diethyl ether (200 ml) and water (200 ml). The organic layer was washed with water, sodium hydroxide (1N), water, and brine; dried over anhydrous magnesium sulfate; filtered; and concentrated in vacuo to give the title compound as an oil (23.6 g, 86%); IR(nujol): no carbonyl; NMR(CDCl₃, TMS): δ1.83(m,2H,CH₂), 2.27(s,3H,ArCH₃), 2.85(t,2H,N=C—CH₂), 2.93(t,2H,S—CH₂); [3.83(s,12%) and 3.95(s,88%),3H,O—CH₃], [6.93-7.2(m,6H) and 7.57(m,2H) aromatic]; mass spectrum m/e 317,286.

C.

4-Fluoro-α-3-(3-methylphenylthio)propyl]benzenemethanamine Hydrochloride

A solution of the methyloxime from part B (16.0 g, 0.050 mole) in dry tetrahydrofuran (50 ml) was cooled in an ice bath and treated with boranetetrahydrofuran complex (1M, 111 ml, 0.111 mole) and stirred at room temperature for 72 hours. The mixture was concentrated in vacuo, and the residue was treated twice with methanol (100 ml) and evaporated. The residue was heated at 80° C. with hydrochloric (6N) acid for one hour and concentrated. The crude product was dissolved in hot water (100 ml) and cooled for 24 hours.

The resulting crystals were collected by filtration, washed with cold water (25 ml) and diethyl ether, and dried to yield the title compound (16.0 g, 97%); mp 189°-190° C.; NMR(DMSO-d$_6$, TMS): δ33,1.52(2m,2H,S—C—CH$_2$), 2.00,2.13(2m,2H,S—C—C—CH$_2$), 2.25(s,3H,ArCH3), 2.93(d of t, 2H,S—CH$_2$), 4.28(t,1H,N—C—H), [6.95-7.33(m,6H) and 7.58(m,2H) aromatic]; Anal. Calcd. for C$_{17}$H$_{20}$FNS.HCl, MW 325.87: C,62.65; H,6.50; N,4.30; S,9.84. Found: C,62.72; H,6.47; N,4.51; S,10.15. Mass spectrum m/e 289/124.

EXAMPLE 3

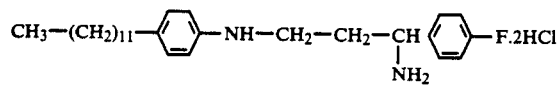

4-Fluoro-α-[3-(4-dodecylphenylamino)propyl]benzenemethanamine Dihydrochloride

A.
3-[(4-Dodecylphenyl)-amino]-1-(4-fluorophenyl)-1-propanone Hydrochloride.

A mixture of 4-dodecylaniline (26.2 g, 0.1 mole) and 3-chloro-4'-fluoropropiophenone (18.7 g, 0.1 mole) in diethyl ether (200 ml) was stirred for 16 hours at room temperature. The mixture was treated with triethylamine (10.1 g, 0.1 mole), stirred for an additional 72 hours, and concentrated in vacuo. The residue was partitioned between diethyl ether (200 ml) and hydrochloric acid (1N, 200 ml). The organic layer was washed with water and brine, dried over anhydrous magnesium sulfate, filtered, and concentrated to an impure tacky solid (41.9 g). A small portion (5 g) was recrystallized from ethanol to give the title compound (4.0 g); mp 107°-109° C.; IR(nujol) C=O @ 1674 cm$^{-1}$; NMR(DMSO-d$_6$, TMS): δ0.5-1.7(m,23H,C$_{11}$H$_{23}$), 2.50(t,2H,ArCH$_2$), 3.30(m,4H, N—CH$_2$—CH$_2$), 6.50,7.00(2d,4H,p-N-phenyl), [7.37(d of d,2H) and 8.07(m,2H) p-F-phenyl]; Anal. Calcd. for C$_{27}$H$_{38}$FNO.HCl, MW 448.05: C,73.37; H,8.77; N,3.19. Found: C,73.09; H,8.50; N,3.19. Mass spectrum m/e 411,284.

B.
4-Fluoro-α-[3-(4-dodecylphenylamino)propyl]benzenemethanamine Dihydrochloride The crude ketone from part A (39.4 g, <0.088 mole) and hydroxylamine hydrochloride (12.3 g, 0.177 mole) in pyridine ethanol (1:1,150 ml) was stirred for 16 hours at room temperature and concentrated in vacuo. The residue was partitioned between methylene chloride (200 ml) and sodium hydroxide (1N 200 ml). The organic layer was washed with water and brine, dried over anhydrous magnesium sulfate, filtered, and concentrated to an impure oil. IR(neat) showed no carbonyl. The oxime was reduced as described in Example 1 and isolated as the "free base". A small portion (5 g) of the free base was converted to the hydrochloride salt and column chromatographed over silica gel (chloroform-methanol, 9:1). Appropriate fractions were combined and concentrated to give an amorphous solid of the title compound (2.6 g); mp 100°-102° C.; NMR(CDCl$_3$, TMS): δ0.5-1.9(m,24H), 2.9-3.5(m,4H,CH$_2$—N—CH$_2$), 5.10(t,1H,N—C—H), 6.9-7.7(m,8H,aromatic); Anal. Calcd. for C$_{27}$H$_{41}$FN$_2$.2HCl, MW 485.54: C,66.78; H,8.93; N,5.77. Found: C,66.72; H,8.82; N,5.32. Mass spectrum m/e 412,150.

EXAMPLE 4

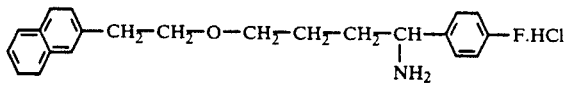

4-Fluoro-α-(3-[2-(2-naphthalenyl)ethoxy]-propyl)benzenemethanamine Hydrochloride

A.
1-(4-Fluorophenyl)-4-[2-(2-naphthalenyl)ethoxy]-1-butanone

A suspension of 4-chloro-4'-fluorobutyrophenone-2,2-dimethylpropylene ketal (28.7 g, 0.1 mole) and sodium hydride (2.6 g, 0.11 mole) in dry N,N-dimethylformamide (50 ml) was treated dropwise with a solution of 2-naphthaleneethanol (17.2 g, 0.1 mole) in dry N,N-dimethylformamide (50 ml). The reaction mixture was stirred at room temperature for one hour and refluxed under dry nitrogen for 16 hours. The mixture was concentrated in vacuo, and the residue was partitioned between diethyl ether (200 ml) and sodium bicarbonate (5%, 200 ml). The organic layer was washed with brine, dried over anhydrous magnesium sulfate, filtered, and concentrated to an impure oil as indicated by tlc (chloroform-methanol, 9:1). The impure ketal was dissolved in methanol (100 ml) and treated with concentrated hydrochloric acid (50 ml) and stirred at room temperature until no starting ketal was evidenced by tlc (chloroform-methanol, 9:1). The reaction mixture was diluted with water (200 ml) and extracted with diethyl ether (200 ml). The ethereal extract was washed with brine, dried over anhydrous magnesium sulfate, filtered, and concentrated to an oil. The oil was column chromatographed on silica gel (n-butyl chloride). Appropriate fractions were combined and concentrated in vacuo to give a solid which was recrystallized from ethanol to yield the title compound (21.2 g, 63%); mp 68°-70° C.; IR(nujol): C=O @ 1679 cm$^{-1}$; NMR(CDCl$_3$, TMS): δ2.0(d of t,2H,CH$_2$), 2.93(t,2H,CH$_2$—CO), 3.03(t,2H,ArCH$_2$), 3.53,3.73(2t,4H,CH$_2$—O—CH$_2$), 6.9-8.0(m,11H,aromatic); Anal. Calcd. for C$_{22}$H$_{21}$FO$_2$, MW 336.40: C,78.55; H,6.92. Found: C,78.18; H,6.33. Mass spectrum m/e 336,154.

B.
1-(4-Fluorophenyl)-3-[2-(2-naphthalenyl)ethoxy]-1-butanone-O-methyloxime

The title compound was prepared from the ketone prepared in A as described in Example 1 as a pure oil (14.5 g,94%); IR(neat): no carbonyl; NMR(CDCl$_3$, TMS): δ1.80(m,2H,CH$_2$), 2.77(t,2H, N=C—CH$_2$), 3.03(t,2H,ArCH$_2$), 3.43,3.67(2t,4H,CH$_2$—O—CH$_2$), 3.93,3.97(2s,3H,O—CH$_3$), 6.7-7.9(m,11H,aromatic).

C.
4-Fluoro-α-3-[2-(2-naphthalenyl)ethoxy]propyl)benzenemethanamine Hydrochloride The title compound was prepared from the methyloxime prepared in B by the method described in Example 1 in 81% yield; mp 122°-124° C.; NMR(DMSO-d$_6$, TMS): δ1.25(m,2H,O—C—CH$_2$), 1.90(m,2H,N—C—CH$_2$), 2.83(t,2H,ArCH$_2$), 3.33,3.60(2t,4H,CH$_2$—O—CH$_2$), 4.22(t,1H,N—C—H), 7.15-7.92(m,11H, aromatic); Anal. Calcd. for C22H24FNO.HCl, MW 373.89: C,70.67; H,6.74; N,3.75. Found: C,70.60; H,6.73; N,3.72. Mass spectrum m/e 337.

EXAMPLE 5

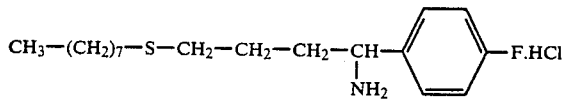

4-Fluoro-α-[3-(octylthio)propyl]benzenemethanamine Hydrochloride

A. 1-(4-Fluorophenyl)-4-(octylthio)-1-butanone

A mixture of 4-chloro-4'-fluorobutyrophenone-2,2 dimethyl propylene ketal (20.0 g, 0.07 mole), octanethiol (10.2 g, 0.07 mole), potassium carbonate (13.8 g, 0.1 mole), and potassium iodide (1 g) in N,N-dimethylformamide (150 ml) was heated at reflux for six hours and concentrated in vacuo. The residue was partitioned between diethyl ether (200 ml) and water (200 ml). The organic layer was washed with water and brine, dried over magnesium sulfate, filtered, and concentrated to an oil. The oil was dissolved in methanol (150 ml), treated with concentrated hydrochloric (50 ml), and refluxed for four hours. The mixture was diluted with water (200 ml) and extracted with diethyl ether (2×150 ml). The ether extracts were combined, washed with water (500 ml) and brine, dried over anhydrous magnesium sulfate, filtered, and concentrated in vacuo to an oil of constant weight to yield the title compound (20.0 g, 93%); IR(neat): C=O @ 1687 cm$^{-1}$; NMR(CDCl$_3$, TMS): δ 0.87(t,3H,CH$_3$), 1.25(m,12H, C$_6$H$_{12}$), 1.57(m,2H,CH$_2$), 2.05(m,2H,S—C—CH$_2$), 2.50(t,2H,CH$_2$—CO), 2.60(t,2H,S—CH$_2$), 3.08(t,2H,S—CH$_2$), [7.10(d of d,2H) and 8.0(m,2H), p-F-phenyl]. Anal. Calcd. for C$_{18}$H$_{27}$FOS, MW 310.47: C,69.63; H,8.77; S,10.33. Found: C,69.17; H,8.49; S,10.55. Mass spectrum m/e 310,143.

B. 1-(4-Fluorophenyl)-4-(octylthio)-1-butanone-O-methyloxime

The title compound (14.1 g, 99%) was prepared from the corresponding ketone prepared in A, according to the method described in Example 1; IR(neat): no carbonyl; NMR(CDCl$_3$, TMS): δ 0.87(t,3H,CH$_3$), 1.25(m,10H,C$_5$H$_{10}$), 1.78(m,2H,N=C—C—CH$_2$), 2.47(t,2H,N=C—CH$_2$), 2.83(t,2H,S—CH$_2$), 3.97(s,3H,O—CH$_3$), [7.05(d of d, 2H) and 7.63(m,2H), p-F-phenyl]. Anal. Calcd. for C$_{19}$H$_{30}$FNOS, MW 339.51: C,67.21; H,8.91; N,4.13; S,9.45. Found: C,67.27; H,8.82; N,4.14; S,10.01. Mass spectrum m/e 339,308.

C. 4-Fluoro-α-[3-(octylthio)propyl]benzenemethanamine Hydrochloride

The title compound (5.3 g, 59%) was prepared from the methyloxime of part B, by the method described in Example 1; mp 143°-146° C.; NMR(CDCl$_3$, TMS): δ 0.88(t,3H,CH$_3$), 1.1-1.6(m,14H, C$_6$H$_{12}$+S—C—CH$_2$), 2.08(m,2H, S—C—CH$_2$), 2.40(m,4H,CH$_2$—S—CH$_2$), 4.17(m,1H,N—C—H), [7.03(d of d,2H) and 7.42(m,2H), p-F-phenyl]; Anal. Calcd. for C$_{18}$H$_{30}$FNS.HCl, MW 347.96: C,62.13; H,8.98; N,4.03; S,9.22. Found: C,62.57; H,8.98; N,4.00; S,9.51. Mass spectrum m/e 311,295,124.

EXAMPLE 6

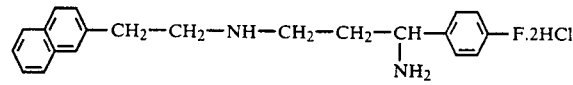

4-Fluoro-α-(2-[2-(2-naphthalenyl)ethylamino]ethyl)-benzenemethanamine Dihydrochloride

1-(4-Fluorophenyl)-3-[2-(2-naphthalenyl)ethylamino]-1-propanone Hydrochloride A1. A solution of 2-naphthaleneethylamine hydrochloride (20.8 g, 0.1 mole) and sodium hydroxide (4.4 g, 0.11 mole) in tetrahydrofuran-water (3:1; 100 ml) was treated dropwise with a solution of 3-chloro-4'-fluoropropiophenone (18.7 g, 0.1 mole) and stirred at room temperature for 16 hours. The mixture was treated with hydrochloric acid (1N) and concentrated in vacuo. The residue was triturated with water (400 ml), and the resulting solid was collected by filtration, washed with water and diethyl ether, and dried. The product was recrystallized from ethanol to yield the title compound (25.5 g, 71%); mp 206.5°-208° C.; IR(nujol): C=O @ 1680 cm$^{-1}$; NMR(DMSO-d$_6$, TMS): δ 3.1-3.9(m,8H,C-H$_2$—CH$_2$—N—CH$_2$—CH$_2$), 7.0-8.2(m,11H,aromatic). Anal. Calcd. for C$_{21}$H$_{20}$FNO.HCl, MW 357.85: C,70.48; H,5.96; N,3.92. Found: C,70.39; H,6.01; N,3.93. Mass spectrum m/e 321.

A2. A solution of 3-chloro-4'-fluoropropiophenone (9.3 g, 0.05 mole) in 100 ml THF was treated with triethylamine (5.6 g, 0.055 mole) and stirred at room temperature for one hour. The mixture was treated with 2-naphthaleneethylamine hydrochloride (10.4 g, 0.05 mole) and refluxed for six hours. The reaction mixture was cooled to room temperature, and the resulting crystals were collected by filtration, washed with THF, ether, and water; and dried to give the title compound as a homogeneous product by tlc (chloroform-methanol, 9:1) (96%, 17.2 g); mp 208°-210° C.; IR(nujol): C=O @ 1675 cm$^{-1}$; NMR(DMSO-d$_6$, TMS): δ 3.20(t,2H, CH$_2$—CO), 3.37(m,4H,Ar—CH$_2$—CH$_2$), 3.60(t,2H,N—CH$_2$) [7.3-7.6(m,5H), 7.7-7.8(m,2H), 8.10(m,2H) aromatic]; Anal. Found: C,70.37; H,5.92; N,3.81. Mass spectrum m/e 321,184.

A3. A mixture of naphthaleneethylamine hydrochloride (11.4 g, 0.055 mole), formalin (3.0 g, 0.1 mole), and 4-fluoroacetophenone (6.9 g, 0.05 mole) in 50 ml of EtOH was refluxed for 24 hours. The mixture was diluted with 200 ml of 1N HCl, and the resulting solid was collected by filtration, washed with a mixture of THF-Et$_2$O (1:1), and dried. The solid was recrystallized from EtOH to yield the title compound (6.2 g, 32%); mp 208°-210° C.

B. 1-(4-Fluorophenyl)-3-[2-(2-naphthalenyl)ethylamino]-1-propanone-O-methyloxime Hydrochloride A mixture of the ketone (15.0 g, 0.042 mole) prepared in A, and methoxylamine hydrochloride (5.25 g, 0.063 mole) in Py-EtOH (1:1, 150 ml) was heated at reflux for 24 hours and concentrated in vacuo. The residue was digested with cold water (200 ml) and collected by filtration. The product was washed with more cold water and dried to yield the title compound (15.0 g, 92%); mp 168°-170° C.; IR(nujol): no carbonyl; NMR(DMSO-d$_6$, TMS): δ 3.0-3.8(m,8H,CH$_2$—CH$_2$—N—CH$_2$—CH$_2$), 3.93(s,3H,O—CH$_3$), 7.1-8.0(m,11-H,aromatic); mass spectrum m/e 351(M+1).

C.
1-(4-Fluorophenyl)-N3-[2-(2-naphthalenyl)ethyl]-1,3-propanediamine Dihydrochloride A suspension of the methyloxime (11.3 g, 0.029 mole) prepared in B in dry THF (50 ml) was cooled in an ice bath and slowly treated with BH$_3$.THF (1M, 75 ml) and heated at reflux for 24 hours and concentrated in vacuo. The residue was carefully treated with methanol (100 ml) and evaporated. The residue was stirred with NaOH (3N,200 ml) for one hour and extracted with CH$_2$Cl$_2$ (300 ml). The extract was washed with water and brine, dried over MgSO$_4$, filtered, and concentrated to an oil. The oil was diluted with Et$_2$O (200 ml) and HCl-Et$_2$O(2N) was added until no further precipitation was observed. The precipitate was collected by filtration, washed with Et$_2$O, and recrystallized from EtOH to yield the title compound (11.0 g, 95%); mp 264°-265° C.; NMR(DMSO-d$_6$, TMS): δ [2.37,2.73, 2.97(3m,4H), 3.17(m,2H, CH$_2$—CH$_2$—N—CH$_2$—CH$_2$), 4.58(T,1H, N—C—H), 7.2-8.0(M,11H,aromatic)]; Anal. Calcd. for C$_{21}$H$_{23}$FN$_2$.2HCl, MW 395.54: C,63.80; H,6.37; N,7.09. Found: C,63.88; H,6.38; N,7.07; mass spectrum m/e 322,181.

EXAMPLE 7

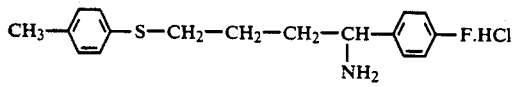

4-Fluoro-α-[3-(4-methylphenylthio)propyl]benzenemethanamine Hydrochloride

A.
1-(4-Fluorophenyl)-4-(4-methylphenylthio)-1-butanone

The title compound (58.0 g, 100%) was prepared from 4-thiocresol and 4-chloro-4'-fluorobutyrophenone as described in Example 2 as an oil; IR(neat): C=O @ 1700 cm$^{-1}$; NMR(DMSO-d$_6$, TMS): δ 1.8-1.95(m,2H, CH$_2$), 2.26(s,3H,ArCH$_3$), 2.98(t,2H,CH$_2$—CO), 3.16(t,2H,S—CH$_2$), 7.1-8.1(m,8H, aromatic); mass spectrum m/e 288.

B.
1-(4-Fluorophenyl)-4-(4-methylphenylthio)-1-butanone-O-methyloxime

The title compound (25.5 g 93%) was prepared from the ketone prepared in A, as described in Example 2, as an oil; IR(neat): no carbonyl; NMR(DMSO-d$_6$, TMS): δ 1.5-1.7(m,2H,CH$_2$), 2.26(s,3H,ArCH$_3$), 2.7-3.0(m,4H, S—CH$_2$ and N=C—CH$_2$), 3.89(s,3H,O—CH$_3$), 7.0-7.7(m,8H,aromatic); mass spectrum m/e 317.

C1.
4-Fluoro-α-[3-(4-methylphenylthio)propyl]benzenemethanamine Hydrochloride The amine hydrochloride (10.0 g, 96%) was prepared from the methyloxime prepared in B, as described in Example 2; mp 176°-178° C.; NMR (DMSO-d$_6$, TMS): δ 1.25,1.43(2m,2H,CH$_2$), 1.97,2.10(2M,2H, N—C—CH$_2$), 2.23(s,3H,ArCH$_3$), 2.87(t,2H,S—CH$_2$), 4.23(t,1H, N—C—H), 7.0-7.57(m,8H,aromatic); Anal. Calcd. for C$_{17}$H$_{20}$FNS.HCl, MW 325.88: C,62.65; H,6.50; N,4.30; S,9.84. Found: C,62.25; H,6.47; N,4.31; S,9.54. Mass spectrum m/e 289.

C2. A mixture of the ketone (21.5 g, 0.075 mole) prepared in A, formamide (13.4 g, 0.3 mole), and 88% formic acid (10.3 g) was refluxed for 24 hours. The mixture was treated with HCl (6N, 100 ml) and refluxed for an additional six hours. The mixture was made alkaline with the addition of NaOH (3N) and extracted with ether (200 ml). The ether extract was washed with water and brine, dried over MgSO4, and filtered. The filtrate was treated with 1.1 equivalents of HCl-Et$_2$O (3N) and placed in the cold. The resulting solid was collected by filtration and dried to yield the title compound, (2.5 g, 10%), mp 182°-184° C., NMR(DMSO-d$_6$, TMS): δ 1.27,1.47(2m,2H,CH$_2$), 1.8-2.17(m,2H, N—C—CH$_2$), 2.25(s,3H,ArCH$_3$), 2.88(t,2H,S—CH$_2$), 4.25(t,1H, N—C—H), 7.0-7.58(m,8H, aromatic); Anal. Found: C,62.54; H,6.41; N,4.33; S,9.89. Mass spectrum m/e 289.

C3. A mixture of the ketone (18.0 g, 0.06 mole) prepared in A, and ammonium acetate (0.1 mole) in EtOH (50 ml) and AcOH (20 ml) was treated with sodium cyanoborohydride (0.1 mole) and stirred at room temperature for 16 hours. The mixture was concentrated in vacuo, and carefully digested with HCl (6N, 200 ml). The mixture was cooled in an ice bath, and the resulting crystals were collected by filtration, washed with cold water and ether, and dried to yield the title compound (9.2 g, 45%); mp 185°-186° C.; tlc homogeneous (CHCl$_3$-MeOH, 9:1); mass spectrum m/e 289.

EXAMPLE 8

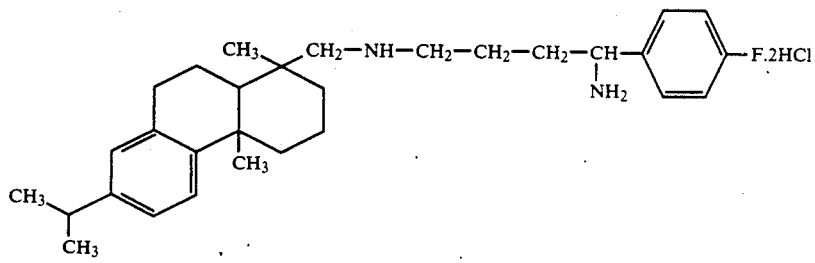

4-Fluoro-α-(4-[1,4a-dimethyl-7-(2-propyl)-
1,2,3,4,4a,9,10,10a-octahydro-1-phenanthrenylme-
thylamino]propyl)-benzenemethanamine
Dihydrochloride

A.

4-([1,4A-Dimethyl-1,2,3,4,4a,9,10,10a-octahydro-7-(1-
methylethyl)-1-phenanthrenyl]methylamino)-1-(4-
fluorophenyl)-1-butanone 4-Methylbenzene sulfonic
acid salt A mixture of 4-chloro-4'-fluorobutyrophenone-2,2-dimethylpropylene ketal (28.7 g, 0.1 mole), dehydroabietylamine (28.5 g, 0.1 mole), potassium carbonate (48 g, 0.35 mole), and potassium iodide (1 g) in DMF (200 ml) was heated at reflux for 24 hours and concentrated in vacuo. The residue was partitioned between ether (300 ml) and water (200 ml). The organic phase was washed with brine, dried over MgSO4, filtered, and concentrated in vacuo to an oil. The oil was dissolved in MeOH (300 ml) and conc. HCl (50 ml) and stirred until no ketal was evidenced by tlc (CHCl3-MeOH, 9:1). The organic solvent was removed in vacuo, and the aqueous phase was made alkaline (pH 8) with 2N NaOH. The mixture was extracted with CH2Cl2 (300 ml). The organic phase was washed with water and brine, dried over MgSO4, filtered, treated with p-toluene sulfonic acid monohydrate, and concentrated in vacuo. The residue was triturated with ether (400 ml), and the resulting solid was collected by filtration, washed with ether, and dried to yield the title compound (43.3 g, 70%); mp 166°–167° C.; IR(nujol): C=O @ 1687 cm$^{-1}$; NMR(CDCl3, TMS): 35 aliphatic protons and 11 aromatic protons; Anal. Calcd. for C30H40FNO.C7H8O3S, MW 621.85: C,71.46; H,7.78; N,2.25; S,5.16. Found: C,71.63; H,7.93; N,2.18; S,5.23. Mass spectrum (FAB) m/e 450 (M+1); [α]$_D^{25}$ +20.3(c,1.05,MeOH).

B.

4-([1,4a-Dimethyl-7-(1-methylethyl)-1,2,3,4,4a,9,10,10a-
octahydro-1-phenanthrenylmethyl]amino)-1-(4-fluoro-
phenyl)-1-butanone O-methyloxime The title compound was prepared as a free base (15.0 g, 97%) from the ketone of part A by the method described in Example 1, as an oil; IR(neat): no carbonyl; NMR(CDCl3, TMS): δ 0.6-3.0(33 aliphatic protons), 3.8,3.93(2s,3H,O—CH3), 6.7–7.7(m,7H, aromatic); mass spectrum m/e 478,191; [α]$_D^{25}$ +19.9° C. (c,0.97,MeOH).

C.

4-Fluor-α-(4-[1,4a-dimethyl-7-(2-propyl)-
1,2,3,4,4a,9,10,10a-octahydro-1-phenanthrenyl-
methylamino]propyl)benzenemethanamine
Dihydrochloride The title compound was prepared from the methoxime of part B as described in Example 1 (11.0 g, 100%); mp 155° C. dec.; NMR(DMSO-d6, TMS): δ 0.5–2.3(m,26H), 2.8(m,6H, CH2—N—CH2—C—CH2), 4.27(t,1H,N—C—H), 6.8–7.18(m,3H,aromatic), [7.28(d of d,2H) and 7.67(m,2H) p-F-phenyl], Anal. Calcd. for C30H43FN2.2HCl, MW 523.61: C,68.82; H,8.66; N,5.35. Found: C,69.32; H,8.62; N,5.05. Mass spectrum m/e 450,368. [α]$_D^{25}$ +4.7° (c,1.02,MeOH).

EXAMPLE 9

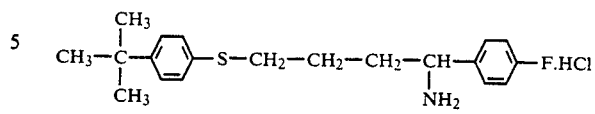

4-Fluoro-α-(3-[4-(1,1-Dimethylethyl)phenylthio]-
propyl)-benzenemethanamine Hydrochloride The title compound was prepared by the method described in Example 2 in 98% yield from the corresponding methyloxime; mp 205°–207° C.

EXAMPLE 10

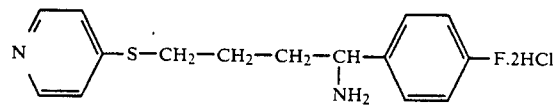

4-Fluoro-α-[3-(4-pyridinylthio)propyl]benzeneme-
thanamine Dihydrochloride

The compound was prepared as described in Example 2 in 69% yield from the corresponding methyloxime; mp 151° C. dec.

EXAMPLE 11

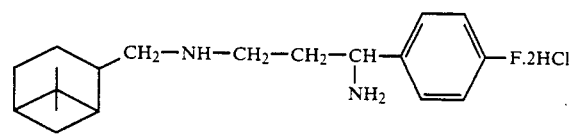

4-Fluoro-α-(2-[(1α,2α,5α-7,7-dimethylbicyclo[3.1.1]-
heptanyl-2-methyl)amino]ethyl)benzenemethanamine
Dihydrochloride The compound was prepared as described in Example 1 and isolated after fractional crystallization to give the product in 40% yield from the corresponding methyloxime; mp 254°–255° C.; [α]$_D^{25}$ −6.82(c,1.03,MeOH).

EXAMPLE 12

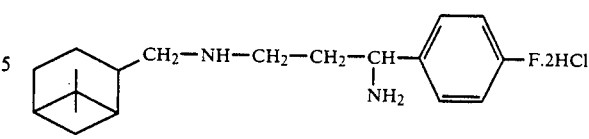

4-Fluoro-α-(2-[(1α,2α,5α-7,7-dimethylbicyclo[3.1.1]-
heptanyl-2-methyl)amino]ethyl)benzenemethanamine
Dihydrochloride The compound of Example 11 was prepared as described in Example 1 and isolated after fractional crystallization as a different diastereomeric mixture from that of Example 11 in 36% yield from the methyloxime; mp 260°–261° C.; [α]$_D^{25}$ −17.3(c,1.07,MeOH).

EXAMPLE 13

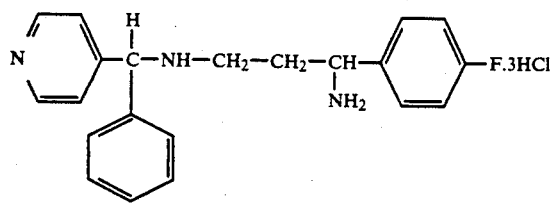

4-Fluoro-α-(2-[1-phenyl-1-(4-pyridinyl)methylamino]ethyl)benzenemethanamine Trihydrochloride The title compound was prepared by the method described in Examples 6A,B,C and isolated as a mixture of diastereomers in 98% yield from the corresponding methyloxime; mp 183° C. dec.

EXAMPLE 14

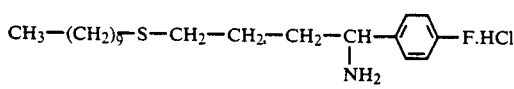

4-Fluoro-α-[3-(decylthio)propyl]benzenemethanamine Hydrochloride

The title compound was prepared as described in Example 5 in 97% yield from the corresponding methyloxime; mp 120°–122° C.

EXAMPLE 15

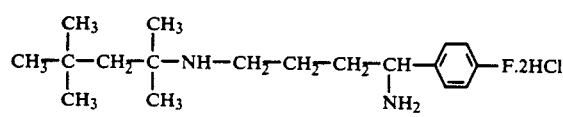

4-Fluoro-α-[3-(1,1,3,3-tetramethylbutyl)aminopropyl]benzenemethanamine Dihydrochloride The title compound was prepared as described in Example 8 in 59% yield from the corresponding methyloxime; mp 139° C. dec.

EXAMPLE 16

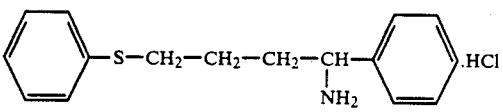

α-[3-(phenylthio)propyl]benzenemethanamine Hydrochloride

The title compound was prepared by the procedure described in Example 2 in a yield of 92% from the corresponding methyloxime; mp 129°–132° C.

EXAMPLE 17

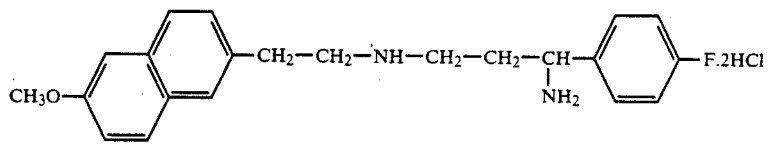

4-Fluoro-α-(2-[(6-methoxy-2-naphthalenyl)ethylamino]ethyl)benzenemethanamine Dihydrochloride The title compound was prepared as described in Example 6 in 84% yield from the corresponding methyloxime; mp 249°–250° C.

EXAMPLE 18

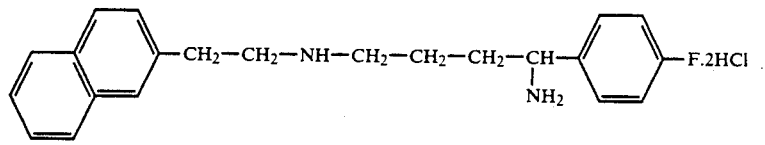

4-Fluoro-α-(3-[(2-naphthalenyl)ethylamino]propyl)benzenemethanamine Dihydrochloride The title compound was prepared as described in Example 8 in 38% yield from the corresponding methyloxime; mp 183°–185° C.

EXAMPLE 19

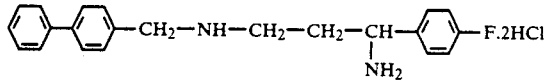

4-Fluoro-α-(2-[(4-biphenyl)methylamino]ethyl)benzenemethanamine Dihydrochloride

The title compound was prepared as described in Example 1 in 100% yield from the corresponding methyloxime; mp 246°–248° C.

EXAMPLE 20

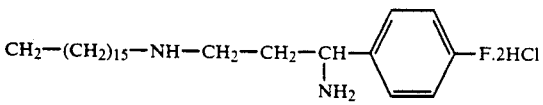

4-Fluoro-α-[2-(hexadecylamino)ethyl]benzenemethanamine Dihydrochloride

The title compound was prepared as described in Example 1 in 90% yield from the corresponding methyloxime; mp 246° C. dec.

EXAMPLE 21

$$CH_3-(CH_2)_7-NH-CH_2-CH_2-CH(NH_2)-C_6H_4-F \cdot 2HCl$$

4-Fluoro-α-[2-(octylamino)ethyl]benzenemethanamine Dihydrochloride

The title compound was prepared as described in Example 1 in 52% yield from the corresponding methyloxime; mp 222°-224° C.

EXAMPLE 22

$$\text{(4-methoxynaphthalenyl)}-CH_2-NH-CH_2-CH_2-CH(NH_2)-C_6H_4-F \cdot 2HCl$$

4-Fluoro-α-(2-[(4-methoxynaphthalenyl)methylamino]ethyl)benzenemethanamine Dihydrochloride The title compound was prepared as described in Example 6 in 67% yield from the corresponding methyloxime; mp 251°-252° C.

EXAMPLE 23

$$\text{(2-CH}_3\text{-C}_6\text{H}_4\text{)}-S-CH_2-CH_2-CH_2-CH(NH_2)-C_6H_4-F \cdot 2HCl$$

4-Fluoro-α-[3-(2-methylphenylthio)propyl]benzenemethanamine Dihydrochloride

The title compound was prepared as described in Example 2 in 97% yield from the corresponding methyloxime; mp 184°-186° C.

EXAMPLE 24

$$CH_3-C_6H_4-S-CH_2-CH_2-CH_2-CH(NH_2)-C_6H_4-F$$

4-Fluoro-α-[3-(4-methylphenylthio)propyl]benzenemethanamine

The corresponding amine hydrochloride was partitioned between diethyl ether and 1N sodium hydroxide. The organic phase was washed with water and brine, dried over magnesium sulfate, filtered, and concentrated to an oil of constant weight in a yield of 99%; IR(neat):NH$_2$ @ 3308,3369 cm$^{-1}$; NMR(CDCl$_3$, TMS): δ 1.2-2.0(m,4H,CH$_2$—CH$_2$), 2.27(s,3H,ArCH$_3$), 2.87(t,2H,S—CH$_2$), 3.77(t,1H,N—C—H), 7.0-7.4(m,8H, aromatic); mass spectrum m/e 289.

EXAMPLE 25

$$CH_3-C_6H_4-S-CH_2-CH_2-CH_2-CH(NH_2)-C_6H_4-F \cdot \begin{array}{c} CO_2H \\ | \\ CHOH \\ | \\ CHOH \\ | \\ CO_2H \end{array}$$

4-Fluoro-α-[3-(4-methylphenylthio)propyl]benzenemethanamine Hemi D-2,3-Dihydroxybutanedioate The amine of Example 24 was dissolved in diethyl ether and treated with 0.5 mole-equivalent of d-tartaric acid. The resulting salt was collected by filtration, washed with diethyl ether and dried to give the title compound in 100% yield; mp 139°-141° C.; Anal. Calcd. for C$_{17}$H$_{20}$FNS·C$_2$H$_3$O$_3$, MW 364.46: C,62.49; H,6.36; N,3.84; S,8.80. Found: C,62.49; H,6.93; N,3.73; S,8.76. Mass spectrum m/e 289 and 150; $[\alpha]_D^{25}$ +13.5° (c,1.00,MeOH).

EXAMPLE 26

$$CH_3-(CH_2)_6-NH-CH_2-CH_2-CH(NH_2)-C_6H_4-F \cdot 2HCl$$

4-Fluoro-α-[2-heptylamino)ethyl]benzenemethanamine Dihydrochloride

The title compound was prepared as described in Example 1 in 85% yield; mp 172°-174° C.

EXAMPLE 27

$$CH_3-(CH_2)_{10}-NH-CH_2-CH_2-CH(NH_2)-C_6H_4-F \cdot 2HCl$$

4-Fluoro-α-[2-(undecylamino)ethyl]benzenemethanamine Dihydrochloride

The title compound was prepared as described in Example 6 in 73% yield from the corresponding methyloxime; mp 200°-203° C.

EXAMPLE 28

$$CH_3-(CH_2)_5-NH-CH_2-CH_2-CH(NH_2)-C_6H_4-F \cdot 2HCl$$

4-Fluoro-α-[2-(hexylamino)ethyl]benzenemethanamine Dihydrochloride

The title compound was prepared as described in Example 1 in 66% yield from the corresponding methyloxime; mp 233°-235° C.

EXAMPLE 29

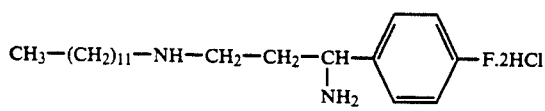

α-[2-(dodecylamino)ethyl]-4-fluoro-benzenemethanamine Dihydrochloride

The title compound was prepared as described in Example 1 in 91% yield from the corresponding methyloxime; mp 243°-245° C.

EXAMPLE 30

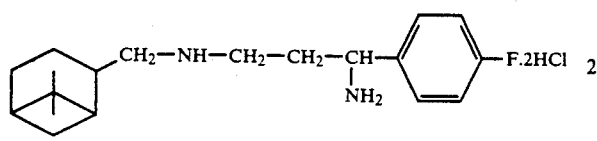

α-[2-(7,7-Dimethylbicyclo[3,1,1]heptyl-2-methylamino)ethyl]-4-fluoro-benzenemethanamine Dihydrochloride The title compound was prepared as described in Example 6A,B,C as a mixture of diastereomers in 94% yield from the corresponding methyloxime; mp >300° C. This example represents a different diastereomeric mixture from those of Examples 11 and 12.

EXAMPLE 31

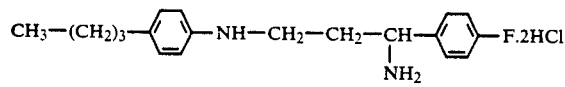

α-(2-[(4-Butylphenyl)amino]ethyl)-4-fluoro-benzenemethanamine Dihydrochloride

The title compound was prepared as described in Example 4 in 98% yield from the corresponding methyloxime; mp 218°-220° C.

EXAMPLE 32

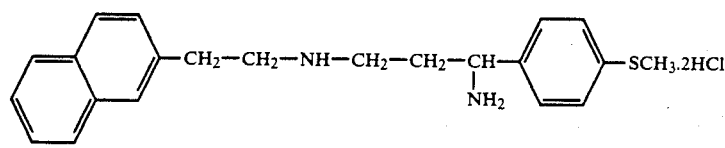

4-Methylthio-α-(2[2-(2-naphthalenyl)ethylamino]ethyl)benzenemethanamine Dihydrochloride The title compound was prepared as described in Example 6A,B,C in 94% yield from the corresponding methyloxime; mp 228°-230° C.

EXAMPLE 33

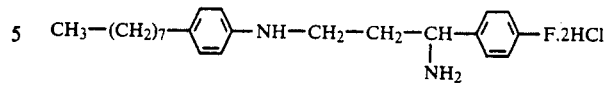

4-Fluoro-α-[2-(4-octylphenylamino)ethyl]benzenemethanamine Dihydrochloride

The title compound was prepared as described in Example 3 in 89% yield from the corresponding methyloxime; mp 220°-222° C.

EXAMPLE 34

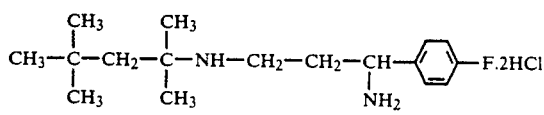

4-Fluoro-α-[2-(1,1,3,3-tetramethylbutyl)aminoethyl]-benzenemethanamine Dihydrochloride The title compound was prepared as described in Example 1 in 100% yield from the corresponding methyloxime; mp 242°-244° C.

EXAMPLE 35

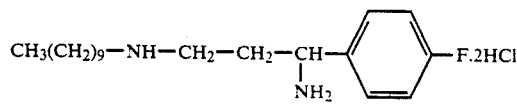

4-Fluoro-α-(2-decylaminoethyl)benzenemethanamine Dihydrochloride

The title compound was prepared as described in Example 1 in 99% yield from the corresponding methyloxime; mp 233°-234° C.

EXAMPLE 36

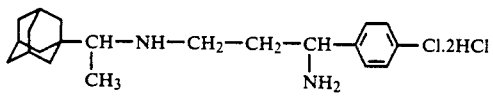

4-Chloro-α-(2-[1-(3-adamantyl)ethylamino]ethyl)benzenemethanamine Dihydrochloride The title compound was prepared as described in Example 6A,B,C in 92% yield from the corresponding methyloxime; mp 189°-194° C.

EXAMPLE 37

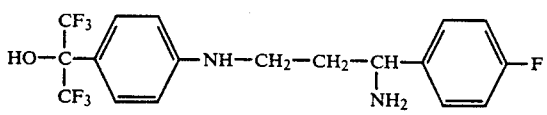

4-Fluoro-α-(2-[4-(1,1,1,3,3,3-hexafluoro-2-hydroxy-prop-2-yl)phenylamino]ethyl)benzenemethanamine The title compound was prepared as described in Example 6A,B,C in 63% yield from the corresponding methyloxime; mp 136°-137° C.

EXAMPLE 38

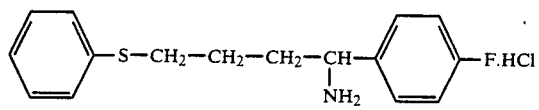

4-Fluoro-α-(3-phenylthiopropyl)benzenemethanamine Hydrochloride

The title compound was prepared as described in Example 2 in 97% yield from the corresponding methyloxime; mp 169°-173° C.

EXAMPLE 39

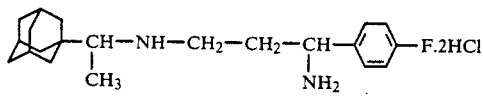

4-Fluoro-α-(2-[1-(3-adamantyl)ethylamino]ethyl)benzenemethanamine Dihydrochloride The title compound was prepared as described in Example 6A,B,C in 98% yield from the corresponding methyloxime; mp 162° C.

EXAMPLE 40

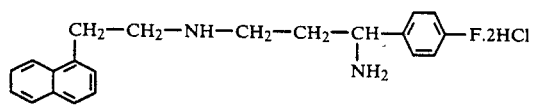

4-Fluoro-α-(2-[2-(1-naphthalenyl)ethylamino]ethyl)-benzenemethanamine Dihydrochloride The title compound was prepared as described in Example 6A,B,C in 94% yield from the corresponding methyloxime; mp 263°-265° C.

EXAMPLE 41

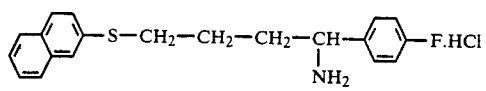

4-Fluoro-α-[3-(2-naphthalenylthio)propyl]benzenemethanamine Hydrochloride

The title compound was prepared as described in Example 2 in 96% yield from the corresponding methyloxime; mp 201°-202° C.

EXAMPLE 42

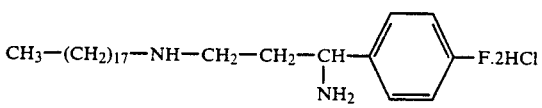

4-Fluoro-α-[2-(octadecylamino)ethyl]benzenemethanamine Dihydrochloride

The title compound was prepared as described in Example 1 in 87% yield from the corresponding methyloxime; mp 248° C. dec.

EXAMPLE 43

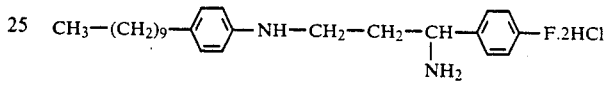

4-Fluoro-α-[2-(4-decylphenylamino)ethyl]benzenemethanamine Dihydrochloride

The title compound was prepared as described in Example 3 in 89% yield from the corresponding methyloxime; mp 208°-210° C.

EXAMPLE 44

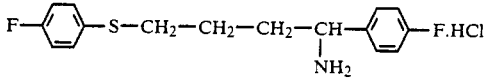

4-Fluoro-α-[3-(4-Fluorophenylthio)propyl]benzenemethanamine Hydrochloride

The title compound was prepared as described in Example 2 in 50% yield from the corresponding methyloxime; mp 122°-123° C.

EXAMPLE 45

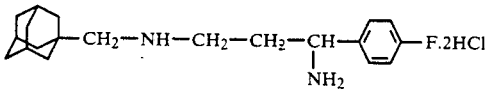

4-Fluoro-α-[2-(3-adamantylmethylamino)ethyl]benzenemethanamine Dihydrochloride

The title compound was prepared as described in Example 1 in 91% yield from the corresponding methyloxime; mp 269°-271° C.

EXAMPLE 46

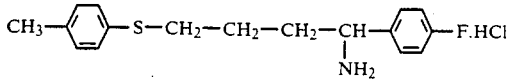

4-Fluoro-α-[3-(4-methylphenylthio)propyl]benzenemethanamine Hydrochloride

The title compound was prepared as described in Example 2 in 93% yield from the corresponding methyloxime; mp 130°-131° C.

EXAMPLE 47

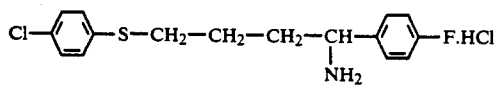

4-Fluoro-α-[3-(4-chlorophenylthio)propyl]benzenemethanamine Hydrochloride

The title compound was prepared as described in Example 2 in 98% yield from the corresponding methyloxime; mp 188°-190° C.

EXAMPLE 48

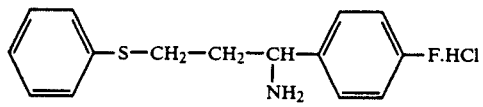

4-Fluoro-α-(2-phenylthioethyl)benzenemethanamine Hydrochloride

The title compound was prepared as described in Example 2 in 44% yield from the corresponding methyloxime; mp 140° C. dec.

EXAMPLE 49

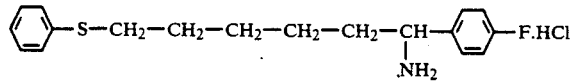

4-Fluoro-α-[5-(phenylthio)pentyl]benzenemethanamine Hydrochloride

The title compound was prepared as described in Example 2 in 99% yield from the corresponding methyloxime; mp 156°-160° C.

EXAMPLE 50

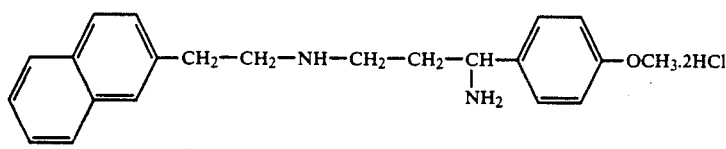

4-Methoxy-α-(2-[2-(2-naphthalenyl)ethylamino]ethyl)-benzenemethanamine Dihydrochloride The title compound was prepared as described in Example 6A,B,C in 98% yield from the corresponding methyloxime; mp 239.5° C. dec.

EXAMPLE 51

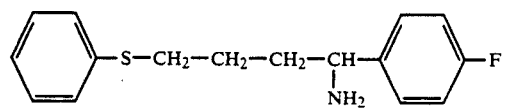

4-Fluoro-α-[3-(phenylthio)propyl]benzenemethanamine

The title compound was prepared as described in Examples 2 and 24, and isolated as an oil in 99% yield from the corresponding methyloxime; IR(neat): NH$_2$@ 3320, 3380 cm$^{-1}$; NMR(CDCl$_3$, TMS): δ1.6(m,2H, CH$_2$—CH$_2$), 2.95(t,2H,S—CH$_2$), 3.83(t,1H,N—C—H), 7.0-7.5(m,9H,aromatic); mass spectrum m/e 275.

EXAMPLE 52

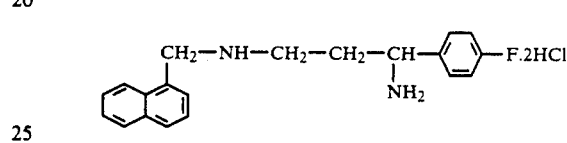

4-Fluoro-α-[2-(1-naphthalenylmethyl)ethylamino]benzene-methanamine Dihydrochloride The title compound was prepared as described in Example 1 in 94% yield from the corresponding methyloxime; mp 245°-248° C.

EXAMPLE 53

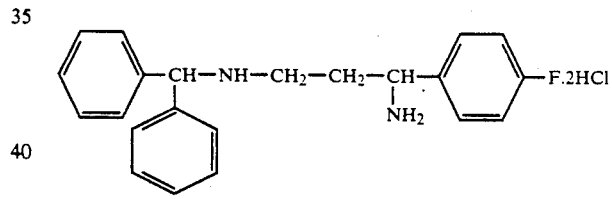

4-Fluoro-α-[2-(Diphenylmethylamino)ethyl]benzenemethanamine Hydrochloride

The title compound was prepared as described in Example 1 in 95% yield from the corresponding methyloxime; mp 248°-251° C.

EXAMPLE 54

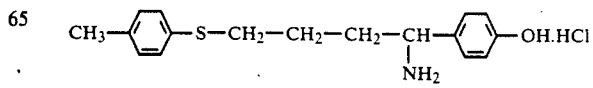

4-Hydroxy-α-[3-(4-methylphenylthio)propyl]benzenemethanamine Hydrochloride

The title compound was prepared as described in Example 2 in 51% yield from the corresponding methyloxime; mp 110° C. dec.

EXAMPLE 55

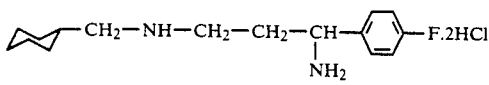

4-Fluoro-α-[2-(Cyclohexylmethylamino)ethyl]benzenemethanamine Dihydrochloride

The title compound was prepared as described in Example 1 in 66% yield from the corresponding corresponding methyloxime; mp 261.0°-261.5° C.

EXAMPLE 56

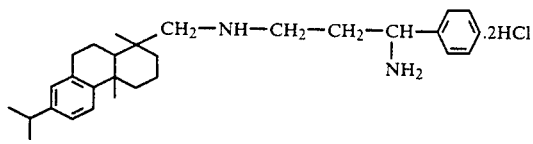

2-(2-[1,4a-Dimethyl-7-(2-propyl)-1,2,3,4,4a,9,10,10a-octahydro-1-phenanthrenylmethylamino]ethyl)benzenemethanamine Dihydrochloride A. The title compound was prepared as described in Example 8 in 41% yield from the corresponding methyloxime after recrystallization from ethanol; mp 262°-264° C.; [α]$_D^{25}$+14.99(c,1.04,MeOH).

B. A different diastereomeric mixture of the title compound was isolated from the ethanol filtrate of "A" and recrystallized from diethyl ether in 33% yield; mp 237°-239° C.; [α]$_D^{25}$+24.68(c,0.93,MeOH).

EXAMPLE 57

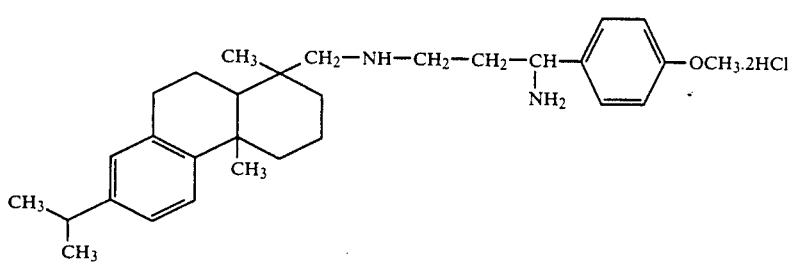

α-(2-[1,4a-Dimethyl-7-(2-propyl)-1,2,3,4,4a,9,10,10a-octahydro-1-phenanthrenylmethylamino]ethyl)-4-methoxybenzenemethanamine Dihydrochloride The title compound was prepared as described in Example 8 in 100% yield from the corresponding methyloxime as a mixture of diastereomers; mp 212° C. dec.; [α]$_D^{25}$+11.52(c,1.02,MeOH).

EXAMPLE 58

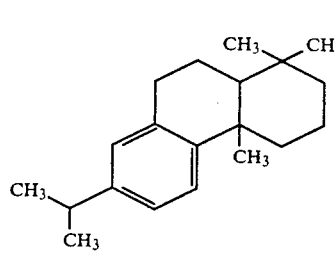

α-(2-[1,4a-Dimethyl-7-(2-propyl)-1,2,3,4,4a,9,10,10a-octahydro-1-phenanthrenylmethylamino]ethyl)-4-methylthio-benzenemethanamine Dihydrochloride The title compound was prepared as described in Example 8 in 76% yield from the corresponding methyloxime as a mixture of diastereomers; mp 210° C. dec.; [α]$_D^{25}$+15.37(c,0.94,MeOH).

EXAMPLE 59

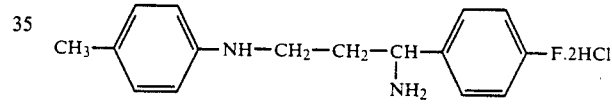

4-Fluoro-α-[2-(4-methylphenylamino)ethyl]benzenemethanamine Dihydrochloride

The title compound was prepared as described in Example 3 in 67% yield; mp 236°-238° C.; Anal. Calcd. for C$_{16}$H$_{19}$FN2.2HCl, MW 331.26: C, 58.01; H, 6.39; N, 8.46. Found: C, 58.22; H, 6.39; N, 8.25. Mass spectrum m/e 258,150.

EXAMPLE 60

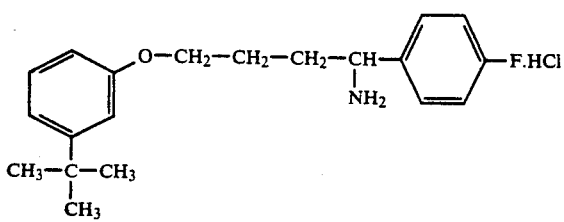

α-[2-(1,1-Dimethylphenyloxy)propyl]-4-fluoro-benzenemethanamine Dihydrochloride

The title compound was prepared as described in Example 4 in 83% yield; mp 187°–190° C.

EXAMPLE 61

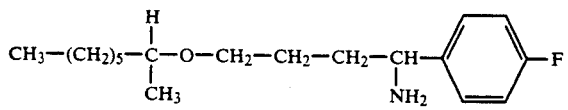

·4-Fluoro-α-[3-(2-octyloxy)propyl]benzenemethanamine

By substituting d-2-octanol in Example 4, the title compound was prepared as a mixture of diastereomers in 99% yield as an oil from the corresponding methyloxime; Anal. Calcd. for $C_{18}H_{30}FNO$, MW 295.43: C, 73.17; H, 10.24; N, 4.74. Found: C, 73.01; H, 10.32; N, 4.69. Mass spectrum m/e 296(M+1).

EXAMPLE 62

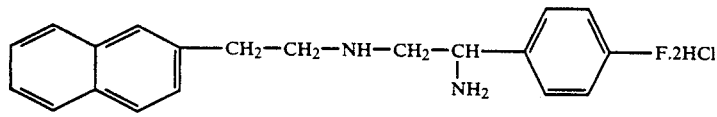

4-Fluoro-α-[(2-naphthalenyl)ethylaminomethyl]benzenemethanamine Dihydrochloride

The title compound was prepared as described in Example 6A, B, C in 61% yield; mp 186°–189° C.; NMR(DMSO-d6, TMS): δ3.0–3.4(m,4H, Ar—CH2—CH2), 3.4–3.8(m,2H,N—CH2), 4.90(t,1H,N—C—H), 7.2–8.0(m,11H,aromatic); Anal. Calcd. for $C_{20}H_{21}FN_2$ HCl, MW 381.31: C, 62.99; H, 6.08; N, 7.35. Found: C, 62.87; H, 6.18; N, 7.57. Mass spectrum m/e 309(M+1).

The compounds prepared according to the procedures illustrated in Examples 1 to 62 are listed in Table I. Dehydroabietyl refers to the group 1,4a-dimethyl-7-(2-propyl)-1,2,3,4,4a,9,10,10a-octahydro-1-phenanthrenylmethyl. Myrtanyl refers to the group 7,7-dimethylbicyclo[3,1,1]heptyl-2-methyl.

EXAMPLE 120

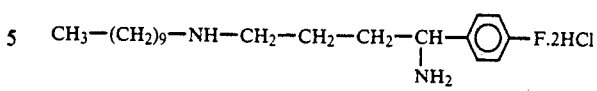

4-Fluoro-α-[3-(decylamino)propyl]benzenemethanamine Dihydrochloride

A mixture of 3-(4-fluorophenyl)propionic acid (19.6 gms, 0.1 mole) and triethylamine (10.1 gms, 0.1 mole) in 150 ml dry methylene chloride was cooled in an ice bath and treated dropwise with ethylchloroformate (10.6 gms, 0.1 mole) in 25 ml dry methylene chloride. The mixture was stirred in the ice bath for one hour and at room temperature for an additional hour. The mixture was then treated with n-decylamine (15.7 gms, 0.1 mole) in 50 ml dry methylene chloride while stirring in an ice bath. The mixture was stirred in the ice bath for one hour and for sixteen hours at room temperature. The reaction mixture was concentrated in vacuo, and the residue was partitioned between 350 ml methylene chloride and 100 ml water. The organic layer was washed with water, 2×100 ml 1N NaOH, water, 2×100 ml 1N HCl, water, and brine; dried over magnesium sulfate; filtered; and concentrated in vacuo. The resulting solid was triturated with 200 ml cold diethyl ether, cooled in an ice bath, and filtered to give the product in 79% (26.4 gms) yield; mp 92.5°–93.5° C.; IR(nujol): N—H @ 3370, C═O @ 1683 and 1642 $cm^{-1}$; NMR(CDCl3, TMS): δ0.88(t,3H,CH3), 1.25(m,14H), 1.50(m,2H, N—C—CH2), 2.60(t,2H,CH2—C═O), 3.25(d of t, 2H,N—CH2), 3.33(t,2H,N—C(O)—CH2), 5.77(broad s,1H,N—H), [7.13(d of d,2H), 8.00(m,2H) p-F-phenyl], Anal. Calcd. for $C_{20} H_{30} N O_2 F$, MW 335.45: C, 71.61; H, 9.01; N, 4.18. Found: C, 71.84; H, 9.05; N, 4.18. Mass spectrum m/e 336(M+1).

A suspension of the above ketoamide (10.0 gms, 0.03 mole) in 80 ml pyridine/abs. ethanol (1:1) was treated with methoxyamine hydrochloride (3.74 gms, 0.045 mole) and stirred for sixteen hours under dry nitrogen at room temperature. The mixture was refluxed for one hour, concentrated in vacuo, cooled in an ice bath, and triturated with 100 ml cold water. The resulting solid was collected by filtration, washed with water, and dried to give the oxime ether in 100% (10.9 gms) yield; mp 71.0° C.; IR(nujol): N—H @ 3287, C═O @ 1648 $cm^{-1}$; NMR(CDCl3 TMS): δ0.88(t,3H,CH3), 1.25(m,14H), 1.43(m,2H,N—C—CH2), 2.40(t,2H,CH2—C═N), 3.03(t,2H,N—C(O)—CH2), 3.18(d of t,2H,N—CH2), [3.83(s,14 units), 3.97(s,149 units), 3H,O—CH3], 5.63(broad s,1H,N—H), [7.03(d of d,2H), 7.63(m,2H)p-F-phenyl].

EXAMPLE 8B

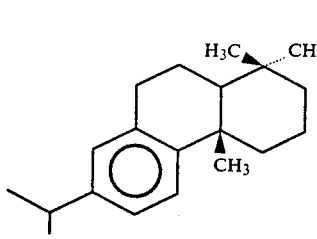

4-Fluoro-α-(4-[1,4A-dimethyl-7-(2-propyl)-
1,2,3,4,4a,9,10,10a-octahydro-1-phenanthrenyl-
methylamino]propyl)benzenemethanamine
Dihydrochloride.

A. A solution of 90% dehydroabietylamine (31.7 g, 0.1 mole), N-hydroxybenzotriazole (13.5 g, 0.1 mole), and 3(p-fluorobenzoyl)propionic acid (19.6 g, 0.1 mole) in 200 ml methylene chloride was cooled in an ice bath and treated with N,N'-dicyclohexylcarbodiimide (20.6 g, 0.1 mole). The mixture was stirred in the ice bath for one hour and six hours at room temperature. The reaction mixture was filtered, and the filtrate was concentrated in vacuo. The residue was dissolved in 200 ml ethyl acetate, allowed to stand at room temperature for one hour, and filtered to remove a small amount of dicyclohexylurea. The filtrate was washed with 2×100 ml 5% sodium bicarbonate, water, 2×100 ml 1N hydrochloric acid, water, and brine; dried over anhydrous magnesium sulfate, filtered, and concentrated to 100 ml. The reddish solution was diluted to the "cloud-point" with petroleum ether and placed in the cold overnight. The resulting solid was collected by filtration, washed with petroleum ether, and dried to give the desired ketoamide in 89.7% (41.6 g) yield; mp 101°–102° C.; IR(nujol): NH @ 3280, C=O @ 1684 and 1665 cm$^{-1}$; NMR(DMSO-d6 TMS): δ0.6–2.1(m, 21H), 2.27("d", 1H,Ar'—CH), 2.55(m,2H,CH$_2$—C=O), 2.78(m,3H,N—CO—CH$_2$+AR'—CH), 3.20(m,3H, CH$_2$—C=O), [6.83(s,1H) 6.95(d,1H) 7.15(d,1H) Ar'], [7.32(d of d,2H), 8.00(m,2H) Ar], and 7.72(t,1H,NH); Anal. Calcd. for C$_{30}$H$_{38}$NO$_2$F, MW 463.61: C, 77.72; H, 8.26; N, 3.02. Found: C, 77.78; H, 8.47; N, 3.09. Mass Spec m/e 464(M+1).

The above oxime ether (12.0 gms, 0.033 mole) was dissolved in 50 ml dry tetrahydrofuran and treated with 100 ml 1M borane-tetrahydrofuran complex and stirred at room temperature for sixteen hours under dry nitrogen. The mixture was then refluxed for four hours, treated with 1N HCl to decompose the excess borane, and concentrated in vacuo. The residue was digested with 100 ml 6N HCl at 80° C. for one hour and cooled in an ice bath. The resulting solid was collected by filtration, washed with cold water, dried, and recrystallized from ethanoldiethyl ether to give the desired diamine hydrochloride in 67% (8.7 gms) yield; mp 181.5°–183.5° C.; NMR (DMSO d6 TMS): δ0.85(t,3H,CH$_3$), 1.23(m,14H), 1.60(m,4H,N—C—CH$_2$ and Ar—C—C—CH$_2$), 1.92,2.05(2m,2H,N—C-*—CH$_2$), 2.78(m,4H,CH$_2$—N—CH$_2$), 4.30(t,1H,N—C-*—H), [7.27(d of d,2H), 7.67(m,2H)p-F-phenyl]; Anal. Calcd. for C$_{20}$H$_{35}$N$_2$F.2HCl, MW 395.44: C, 60.75; H, 9.43; N, 7.08. Found: C, 60.73; H, 9.46; N, 6.92. Mass spectrum m/e 323(M+1).

B. A solution of the above keto-amide (18.5 g, 0.04 mmole) in 50 ml dry pyridine and 50 ml absolute ethanol was combined with methoxylamine hydrochloride (3.7 g, 0.044 mole) and stirred at room temperature for 16 hours, refluxed for three hours, and concentrated in vacuo. The residue was partitioned between 200 ml diethyl ether and 200 ml cold water. The organic layer was washed with water and brine, dried over anhydrous magnesium sulfate, filtered, and concentrated to give the oxime ether in 96% (18.9 g) yield as a gum; IR(CHCl$_3$ film): NH @ 3331, C=O @ 1658 cm$^{-1}$; NMR(CDCl$_3$ TMS): δ0.6–2.1(m,21H), 2.27(d,1H, Ar'CH), 2.40(m,Ar'CH$_2$), 2.83(m,2H,CH$_2$—C=N—), 3.1(m,4H,CH$_2$—N—CH$_2$), 3.93,3.98(2s,3H,O—CH$_3$), 5.57(m,1H,NH), [6.8–7.2(m,5H) and 7.6(m,2H) Ar and Ar'].

C. The above oxime ether (18.9 g, 0.038 mole) was treated with 1M borane-tetrahydrofuran complex (155 ml) and refluxed for 16 hours. The excess borane was decomposed with cold water, and the mixture was concentrated in vacuo. The residue was digested with 100 ml 6N hydrochloric acid for one hour at 80° C. and concentrated in vacuo. The residue was made alkaline with 1N sodium hydroxide and extracted with 200 ml diethyl ether. The organic layer was washed with water and brine, dried over anhydrous magnesium sulfate, filtered, and treated with 100 ml 1N hydrogen chloride/diethyl ether. The resulting white solid was collected by filtration, washed with diethyl ether, dried to give the desired diamine in 82% (17.3 g) yield as a hygroscopic hydrate; mp 165°–168° C.; NMR(DMSO-d6 TMS): δ0.5–2.17(m,25H), 2.27(d,1H, Ar'CH), 2.8(m,6H,CH$_2$—N—CH$_2$) and Ar'CH$_2$), 4.30(m,1H,H—C—N), [6.87(s,1H), 6.95(d,1H), and 7.15(d,1H) Ar'], [7.28(d of d,2H) and 7.67(m,2H), Ar]; Anal. Calcd. for C$_{30}$H$_{43}$N$_2$F.2HCl 1.5 H$_2$O, MW 550.63: C, 65.46; H, 8.79; N, 5.09. Found: C, 65.82; H, 8.80; N, 5.06. Mass spec m/e 451(M+1), [α]+4.6(c, 1.04, MeOH).

EXAMPLE 121

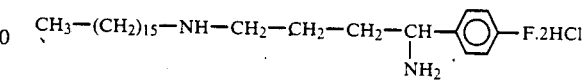

4-Fluoro-α-[3-(n-hexadecylamino)propyl]benzenemethanamine Dihydrochloride

The title compound was prepared as described in Example 120 in 99% yield from the oxime ether; mp 185.0–188.0° C.

EXAMPLE 122

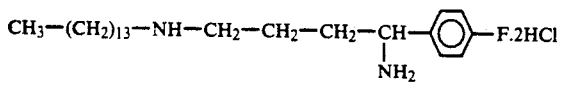

4-Fluoro-α-[3-(n-tetradecylamino)propyl]benzenemethanamine Dihydrochloride

The title compound was prepared as described in Example 120 in 84% yield; mp 227.0°–229.0° C.

EXAMPLE 123

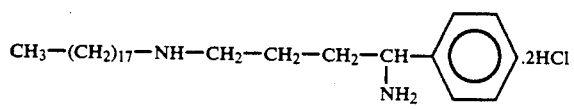

3-(n-Octadecylamino)propyl]benzenemethanamine Dihydrochloride

By substituting 3-benzoylpropionic acid and n-octadecylamine in the method of Example 120, the title compound was obtained in 100% yield from the oxime ether; mp 248°–249° C.

EXAMPLE 124

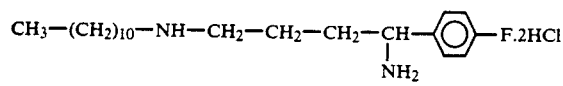

4-Fluoro-α-[3-(n-undecylamino)propyl]benzenemethanamine Dihydrochloride

The desired compound was obtained in 91% yield from the oxime ether using the method described in Example 120; mp 206°–208° C.

EXAMPLE 125

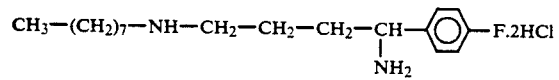

4-Fluoro-α-[3-(n-octylamino)propyl]benzenemethanamine Dihydrochloride

By substituting octyl amine in the method of Example 120, the title compound was obtained in 100% yield from the oxime ether; mp 114°–116° C.

EXAMPLE 126

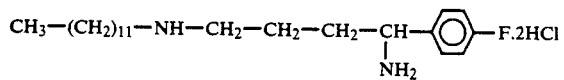

4-Fluoro-α-[3-(n-dodecylamino)propyl]benzenemethanamine Dihydrochloride

The title compound was prepared in 84% yield from the corresponding oxime ether using the procedure described in Example 120; mp 183°–184° C.

EXAMPLE 127

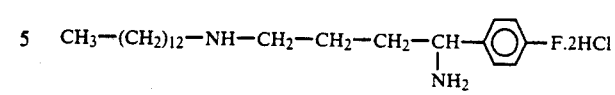

4-Fluoro-α-[3-(n-tridecylamino)propyl]benzenemethanamine Dihydrochloride

The title compound was prepared following the procedure outlined in Example 120 in 52% yield; mp 180°–182° C.

EXAMPLE 128

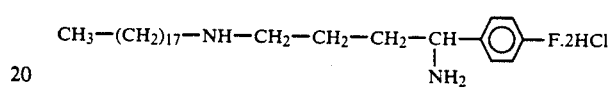

4-Fluoro-α-[3-(n-octadecylamino)propyl]benzenemethanamine Dihydrochloride

The title compound was prepared in 58% yield; mp 154.0°–156.0° C. following the procedure for Example 120.

EXAMPLE 129

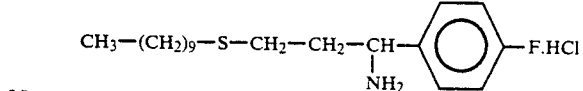

4-Fluoro-α-[2-(n-decylthio)ethyl]benzenemethanamine Hydrochloride

The title compound was prepared as described Example 5 in 88% yield; mp 110°–112° C.

EXAMPLE 130

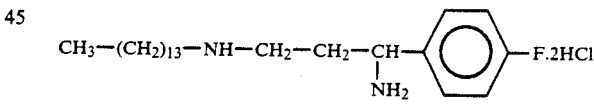

4-Fluoro-α-[2-(n-tetradecylamino)ethyl]benzenemethanamine Dihydrochloride

The title compound was prepared following the procedure described in Example 1 in 68% yield; mp 245° C. dec.

EXAMPLE 131

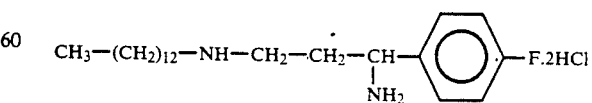

4-Fluoro-α-[2-(n-tridecylamino)ethyl]benzenemethanamine Dihydrochloride

The title compound was prepared as described in Example 1 in 76% yield; mp 226°–228° C.

EXAMPLE 132

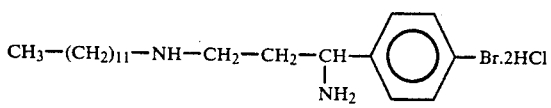

4-Bromo-α-[2-(n-dodecylamino)ethyl]benzenemethanamine Dihydrochloride

The title compound was synthesized using the procedure described in Example 1 in 94% yield from the oxime ether; mp 232° C. dec.

EXAMPLE 133

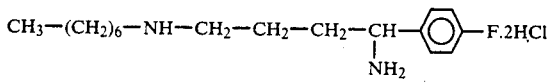

4-Fluoro-α-[3-(n-heptylamino)propyl]benzenemethanamine Dihydrochloride

Using the procedure described in Example 120, the title compound was prepared in 83% yield; mp 204°-206° C.

EXAMPLE 134

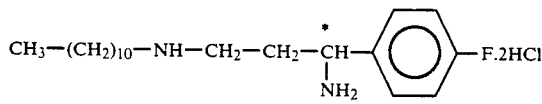

(+)-4-Fluoro-α-[2-(n-undecylamino)ethyl]benzenemethanamine Dihydrochloride

The enantiomerically enriched compound corresponding to the racemic mixture described in Example 27 was prepared by a modification of the method described by Sakito, Suzukamo, and Yoneyoshi, Tetrahedron Letters, Vol. 29, No. 2, pp 223-224, 1988.

The prerequisite ketone and oxime ether were prepared as described in Example 1.

A solution of (1R,2S)-(−)-norephedrine (15.8 gms, 0.104 mole) in 50 ml dry tetrahydrofuran was cooled in an acetonitrile-dry ice bath and treated with 1M borane-tetrahydrofuran complex. The mixture was removed from the bath and stirred at room temperature for one hour. The mixture was recooled in the acetonitrile-dry ice bath and treated with a solution of the oxime ether free base (0.044 mole) in 50 ml dry tetrahydrofuran. The mixture was stirred in the bath for one hour and at room temperature for sixteen hours. The mixture was then refluxed for three hours, cooled to room temperature, treated with 1N hydrochloric acid to decompose the excess borane, and concentrated in vacuo. The residue was digested with 100 ml 6N hydrochloric acid at 80° C. for one hour, and again concentrated in vacuo. The residue was made alkaline with 2N sodium hydroxide and extracted with 3×100 ml diethyl ether. The ether extracts were combined, washed with 1N sodium hydroxide, water, and brine; dried over magnesium sulfate; filtered; and treated with 100 ml 1N hydrogen chloride/diethyl ether. The ether was evaporated in vacuo, and the residue was crystallized twice from warm acetonitrile to give the product in 56% (9.3 gms) yield; mp 191.0°-192.5° C.; NMR(DMSO d6 TMS): δ 0.83(t,3H, $CH_3$), 1.22(m,16H), 1.58(m,2H,N—C—$CH_2$), 2.1-3.0(m,6H,$CH_2$—N—$CH_2$—$CH_2$), 4.52(t,1H,H—C—N), [7.27(d of d, 2H), 7.67(m,2H)p-F-phenyl]. Anal. Calcd. for $C_{20}H_{35}N_2$ F.2HCl, MW 395.43: C, 60.75; H, 9.43; N, 7.08. Found: C, 60.48; H, 9.33; N, 6.88. Mass spectrum m/e 323(M+1); $[\alpha]_D^{25}$+5.6°±0.8° (c,1.OO, MeOH).

EXAMPLE 135

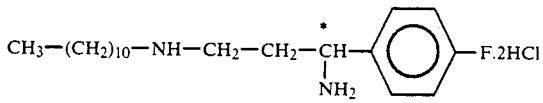

(−)-4-Fluoro-α-[2-(n-undecylamino)ethyl]benzenemethanamine Dihydrochloride

By substituting (1S,2R)-(+)-norephedrine in the method of Example 134, the product was isolated in 55% (7.3 gms) yield; mp 199.0°-200.0° C.; NMR (DMSO d6 TMS): δ 0.83(t,3H,$CH_3$), 1.22(m,16H), 1.57(m,2H,N—C—$CH_2$), 2.1-3.0(m,6H,$CH_2$—N—$CH_2$—$CH_2$), 4.52(t,1H,H—C—N), [7.27(d of d,2H), 7.67(m,2H)p-F-phenyl]. Anal. Calcd. for $C_{20}H_{35}N_2$ F.2HCl, MW 395.43: C, 60.75; H, 9.43; N, 7.08. Found: C, 60.68; H, 9.45; N, 7.20. Mass spectrum m/e 323 (M+1); $[\alpha]_D^{25}$−7.4°±0.8° (c,1.Ol,MeOH).

TABLE I

R—X—$(CH_2)_n$—CH(—$NH_2$)—C₆H₄—Z

| Ex. | R | X | n | z | mp °C. | Yield % |
|---|---|---|---|---|---|---|
| 1 | Dehydroabietyl | NH | 2 | p-F | 215 dec. | 91 |
| 2 | 3-Methylphenyl | S | 3 | p-F | 189-190 | 97 |
| 3 | 4-Dodecylphenyl | NH | 2 | p-F | 100-102 | 90 |
| 4 | 2-Naphthalenylethyl | O | 3 | p-F | 122-124 | 81 |
| 5 | n-Octyl | S | 3 | p-F | 143-146 | 59 |
| 6 | 2-Naphtalenylethyl | NH | 2 | p-F | 264-265 | 95 |
| 7 | 4-Methylphenyl | S | 3 | p-F | 176-178 | 96 |
| 8 | Dehydroabietyl | NH | 3 | p-F | 155 dec. | 100 |
| 9 | 4-t-Butylphenyl | S | 3 | p-F | 205-207 | 98 |
| 10 | 4-Pyridinyl | S | 3 | p-F | 151 dec. | 69 |
| 11 | (−)-cis-Myrtanyl | NH | 2 | p-F | 254-255 | 40 |
| 12 | (−)-cis-Myrtanyl | NH | 2 | p-F | 260-261 | 36 |
| 13 | Phenyl-4-pyridinyl methyl | NH | 2 | p-F | 183 dec. | 98 |
| 14 | n-Decyl | S | 3 | p-F | 120-122 | 97 |

TABLE I-continued

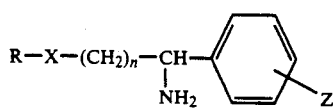

| Ex. | R | X | n | z | mp °C. | Yield % |
|---|---|---|---|---|---|---|
| 15 | t-Octyl | NH | 3 | p-F | 139 dec. | 59 |
| 16 | Phenyl | S | 3 | H | 129–132 | 92 |
| 17 | 6-Methoxy-2-naphthalenyl ethyl | H | 2 | p-F | 249–250 | 84 |
| 18 | 2-Naphthalenylethyl | NH | 3 | p-F | 183–185 | 38 |
| 19 | Biphenyl-4-methyl | NH | 2 | p-F | 246–248 | 100 |
| 20 | n-Hexadecyl | NH | 2 | p-F | 246 dec. | 90 |
| 21 | n-Octyl | NH | 2 | p-F | 222–224 | 52 |
| 22 | 4-Methoxy-1-naphthalenyl ethyl | NH | 2 | p-F | 251–252 | 67 |
| 23 | 2-Methylphenyl- | S | 3 | p-F | 184–186 | 97 |
| 24 | 4-Methylphenyl- | S | 3 | p-F | OIL | 99 |
| 25 | 4-Methylphenyl- | S | 3 | p-F | 139–141 | 100 |
| 26 | n-Heptyl | NH | 2 | p-F | 172–174 | 85 |
| 27 | n-Undecyl | NH | 2 | p-F | 200–203 | 73 |
| 28 | n-Hexyl | NH | 2 | p-F | 233–235 | 66 |
| 29 | n-Dodecyl | NH | 2 | p-F | 243–245 | 91 |
| 30 | (−)-cis-Myrtanyl | NH | 2 | p-F | >300 | 94 |
| 31 | 4-n-Butylphenyl | NH | 2 | p-F | 218–220 | 98 |
| 32 | 2-Naphthalenylethyl | NH | 2 | p-SMe | 228–230 | 94 |
| 33 | 4-n-Octylphenyl | NH | 2 | p-F | 220–222 | 89 |
| 34 | t-Octyl | NH | 2 | p-F | 242–244 | 100 |
| 35 | n-Decyl | NH | 2 | p-F | 233–234 | 99 |
| 36 | 1-Adamantyl-1-ethyl | NH | 2 | p-Cl | 189–194 | 92 |
| 37 | 4-HFI-phenyl | NH | 2 | p-F | 136–137 | 63 |
| 38 | Phenyl | S | 3 | p-F | 169–173 | 97 |
| 39 | 1-Adamantyl-1-ethyl | NH | 2 | p-F | 162 dec. | 98 |
| 40 | 1-Naphthalenylethyl | NH | 2 | p-F | 263–265 | 94 |
| 41 | 2-Naphthalenyl | S | 3 | p-F | 201–202 | 96 |
| 42 | n-Octadecyl | NH | 2 | p-F | 248 dec. | 87 |
| 43 | 4-n-Decylphenyl | NH | 2 | p-F | 208–210 | 89 |
| 44 | 4-Fluorophenyl | S | 3 | p-F | 122–123 | 50 |
| 45 | 1-(3-Adamantylmethyl | NH | 2 | p-F | 269–271 | 91 |
| 46 | 4-Methylphenyl | S | 3 | H | 130–131 | 93 |
| 47 | 4-Chlorophenyl | S | 3 | p-F | 188–190 | 98 |
| 48 | Phenyl | S | 2 | p-F | 140 dec. | 44 |
| 49 | Phenyl | S | 5 | p-F | 156–160 | 99 |
| 50 | 2-Naphthalenylethyl | NH | 2 | p-OMe | 235.5 dec. | 98 |
| 51 | Phenyl | S | 3 | p-F | OIL | 99 |
| 52 | 1-Naphthalenylmethyl | NH | 2 | p-F | 245–248 | 94 |
| 53 | Diphenylmethyl | NH | 2 | p-F | 248–251 | 95 |
| 54 | 4-Methylphenyl | S | 3 | p-OH | 110 dec. | 51 |
| 55 | Cyclohexanemethyl | NH | 2 | p-F | 261–261.5 | 66 |
| 56 | Dehydroabietyl | NH | 2 | H | 237–239 | 41 |
| 57 | Dehydroabietyl | NH | 2 | p-OMe | 212 dec. | 100 |
| 58 | Dehydroabietyl | NH | 2 | p-SMe | 210 dec. | 76 |
| 59 | 4-Methylphenyl | NH | 2 | p-F | 236–238 | 67 |
| 60 | 3-t-Butylphenyl | O | 3 | p-F | 187–190 | 83 |
| 61 | d-2-Octyl | O | 3 | p-F | OIL | 99 |
| 62 | 2-Naphthalenylethyl | NH | 1 | p-F | 186–189 | 61 |

By using the methods described in the preceding examples, other compounds of Formula I can be prepared. Examples of such compounds are listed in Table II.

TABLE II $$R-X-(CH_2)_n-\underset{\underset{Z}{\big|}}{\overset{\overset{NH_2}{\big|}}{CH}}-\text{C}_6\text{H}_4-Z$$

| Ex. | R | X | n | Z | mp °C. | Yield % |
|---|---|---|---|---|---|---|
| 62 | (dehydroabietyl-CH₂) | S | 2 | p-F | | |
| 63 | CH₃(CH₂)₁₁—C₆H₄— | O | 3 | p-F | | |
| 64 | CH₃(CH₂)₁₁—C₆H₄— | S | 3 | p-F | | |
| 65 | CH₃(CH₂)₁₁—C₆H₄— | S | 2 | p-F | | |
| 66 | 2-naphthyl-CH₂—CH₂— | O | 3 | p-SCH₃ | | |
| 67 | 2-naphthyl-CH₂—CH₂— | S | 3 | p-F | | |
| 68 | 2-naphthyl-CH₂—CH₂— | S | 2 | p-F | | |
| 69 | pinanyl-CH₂— | O | 3 | p-F | | |
| 70 | pinanyl-CH₂— | O | 3 | p-SCH₃ | | |
| 71 | pinanyl-CH₂— | O | 3 | p-Br | | |
| 72 | pinanyl-CH₂— | NH | 3 | p-F | | |

TABLE II-continued

R—X—(CH$_2$)$_n$—CH(NH$_2$)—C$_6$H$_4$—Z

| Ex. | R | X | n | Z | mp °C. | Yield % |
|---|---|---|---|---|---|---|
| 73 | pinanyl-CH$_2$— | NH | 3 | pSO$_2$CH$_3$ | | |
| 74 | CH$_3$—(CH$_2$)$_7$-naphthyl-CH$_2$—CH$_2$— | NH | 2 | p-F | | |
| 75 | CH$_3$—(CH$_2$)$_7$-naphthyl-CH$_2$—CH$_2$— | NH | 3 | p-F | | |
| 76 | CH$_3$—(CH$_2$)$_9$-naphthyl-CH$_2$—CH$_2$— | NH | 3 | p-F | | |
| 77 | naphthyl-CH$_2$—CH$_2$— | NH | 3 | p-Br | | |
| 78 | CF$_3$—C$_6$H$_4$—cyclohexyl— | NH | 3 | p-F | | |
| 79 | CF$_3$—C$_6$H$_4$—cyclohexyl— | NH | 3 | p-OCH$_3$ | | |
| 80 | CF$_3$—C$_6$H$_4$—cyclohexyl— | NH | 3 | H | | |
| 81 | CF$_3$—C$_6$H$_4$—cyclohexyl— | NH | 3 | p-SCH$_3$ | | |
| 82 | Cl—C$_6$H$_4$—cyclohexyl— | NH | 2 | p-F | | |
| 83 | Cl—C$_6$H$_4$—cyclohexyl— | S | 2 | p-F | | |

TABLE II-continued $$R-X-(CH_2)_n-\underset{\underset{NH_2}{|}}{CH}-C_6H_4-Z$$

| Ex. | R | X | n | Z | mp °C. | Yield % |
|---|---|---|---|---|---|---|
| 84 | 4-pyridyl-CH(C6H5)– | NH | 3 | p-F | | |
| 85 | 4-pyridyl-CH(C6H5)– | S | 3 | p-F | | |
| 86 | 4-pyridyl-CH(C6H5)– | O | 3 | p-F | | |
| 87 | CH3–(CH2)11–C6H4– | NH | 3 | p-F | | |
| 88 | (CF3)2C(OH)–C6H4– | NH | 3 | p-F | | |
| 89 | (CF3)2C(OH)–C6H4– | NH | 3 | p-SCH3 | | |
| 90 | (CF3)2C(OH)–C6H4– | S | 3 | p-F | | |
| 91 | 4-pyridyl– | S | 3 | p-SCH3 | | |
| 92 | 4-pyridyl– | S | 3 | p-OCH3 | | |
| 93 | 3-CH3-C6H4– | S | 3 | p-OCH3 | | |

TABLE II-continued $$R-X-(CH_2)_n-\underset{\underset{NH_2}{|}}{CH}-C_6H_4-Z$$

| Ex. | R | X | n | Z | mp °C. | Yield % |
|---|---|---|---|---|---|---|
| 94 | 3-methylphenyl | S | 2 | p-F | | |
| 95 | 3-methylphenyl | S | 3 | p-SCH₃ | | |
| 96 | cyclohexyl-CH₂— | NH | 3 | p-SCH₃ | | |
| 97 | 4'-methylbiphenyl-4-CH₂— | NH | 3 | p-F | | |
| 98 | anthracen-2-yl-CH₂— | NH | 2 | p-F | | |
| 99 | anthracen-2-yl-CH₂— | NH | 3 | p-F | | |
| 100 | anthracen-2-yl-CH₂— | S | 3 | p-F | | |
| 101 | anthracen-2-yl-CH₂— | S | 2 | p-SCH₃ | | |
| 102 | anthracen-2-yl-CH₂— | NH | 3 | p-OCH₃ | | |
| 103 | podocarpyl-CH₂— | NH | 3 | p-F | | |
| 104 | dehydroabietyl-CH₂— | NH | 2 | p-SCH₃ | | |

TABLE II-continued

R—X—(CH₂)ₙ—CH(NH₂)—C₆H₄—Z

| Ex. | R | X | n | Z | mp °C. | Yield % |
|---|---|---|---|---|---|---|
| 105 | (abietane-type tricyclic diterpene with CH₂—) | NH | 2 | p-OCH₃ | | |
| 106 | (tricyclic diterpene with CH₂—) | NH | 2 | H | | |
| 107 | (tricyclic diterpene with CH₂—) | NH | 3 | p-F | | |
| 108 | (tricyclic diterpene with CH₂—) | O | 3 | p-F | | |
| 109 | (tricyclic diterpene with CH₂—) | S | 3 | p-F | | |
| 110 | (tricyclic diterpene with CH₂—CH₂—) | NH | 3 | p-F | | |
| 111 | (tricyclic diterpene with CH₂—) | NH | 3 | p-OCH₃ | | |

TABLE II-continued

R—X—(CH₂)ₙ—CH(NH₂)—[phenyl]-Z

| Ex. | R | X | n | Z | mp °C. | Yield % |
|---|---|---|---|---|---|---|
| 112 | (octahydrophenanthrene with CH₂— and isopropyl) | NH | 5 | p-SCH₃ | | |
| 113 | (hexahydrophenanthrene with CH₂— and isopropyl) | NH | 3 | p-SCH₃ | | |
| 114 | (tetrahydrophenanthrene with CH₂ and isopropyl) | O | 3 | p-F | | |
| 115 | (tetrahydrophenanthrene with CH₂ and isopropyl) | S | 3 | p-F | | |
| 116 | (tetrahydrophenanthrene with CH₂ and isopropyl) | NH | 3 | o-Cl | | |
| 117 | (naphthyl-CH₂—CH₂—) | S | 2 | m-Cl | | |
| 118 | (tetrahydrophenanthrene with CH₂ and isopropyl) | NH | 2 | o-Br | | |
| 119 | (naphthyl-CH₂—CH₂—) | S | 3 | m-Br | | |

TABLE II-continued $$R-X-(CH_2)_n-\underset{\underset{NH_2}{|}}{CH}-\underset{Z}{\underset{|}{\bigcirc}}$$

| Ex. | R | X | n | Z | mp °C. | Yield % |
|---|---|---|---|---|---|---|
| 120 | n-Decyl | NH | 3 | p-F | 181.5–183.5 | 100 |
| 86 | Dehydroabietyl | NH | 3 | p-F | 165–168 | 82 |
| 121 | n-Hexadecyl | NH | 3 | p-F | 185–188 | 99 |
| 122 | n-Tetradecyl | NH | 3 | p-F | 227–229 | 84 |
| 123 | n-Octyl | NH | 3 | H | 248–249 | 100 |
| 124 | n-Undecyl | NH | 3 | p-F | 206–208 | 91 |
| 125 | n-Octyl | NH | 3 | p-F | 114–116 | 100 |
| 126 | n-Dodecyl | NH | 3 | p-F | 183–184 | 84 |
| 127 | n-Tridecyl | NH | 3 | p-F | 180–182 | 52 |
| 128 | n-Octadecyl | NH | 3 | p-F | 154–156 | 58 |
| 129 | n-Decyl | S | 2 | p-F | 110–112 | 88 |
| 130 | n-Tetradecyl | NH | 2 | p-F | 245-dec | 68 |
| 131 | n-Tridecyl | NH | 2 | p-F | 226–228 | 76 |
| 132 | n-Dodecyl | NH | 2 | p-Br | 232-dec | 94 |
| 133 | n-Heptyl | NH | 3 | p-F | 204–206 | 83 |
| 134 | n-Undecyl | NH | 2 | p-F | 191–192.5 | 56 |
| 135 | n-Undecyl | NH | 2 | p-F | 199–200 | 55 |

DOSAGE AND DOSAGE FORMS

The phospholipase $A_2$ inhibitors of this invention can be administered to treat inflammatory and/or allergic conditions, including but not limited to rheumatoid arthritis, and other rheumatic disorders, collagen diseases, dermatoses, allergic diseases, chronic obstructive and bronchospastic lung diseases such as asthma and bronchitis. The compounds of this invention may also be useful in the treatment of osteoarthritis.

They may be administered by any means that enables the active agent to reach the agent's site of action in the body of a mammal. They can be administered by any conventional means available for administration of pharmaceuticals, either as individual therapeutic agents or in combination with other therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.1 to 100 milligrams per kilogram of body weight. Ordinarily 0.5 to 50, and preferably 1 to 10 milligrams per kilogram per day given in divided doses 1 to 6 times a day or in sustained release form is effective to obtain desired results.

Dosage forms (compositions) suitable for internal administration contain from about 1 milligram to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms, by inhalation in the form of a nasal spray or lung inhaler, or topically as an ointment, cream or lotion.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain the active ingredient, and, if necessary, suitable stabilizing agents, and/or, buffer substances. Antioxidizing agents such as sodium bisulfite, sodium sulfite, or ascorbic acid either alone or combined are suitable stabilizing agents. Also used are citric acid and its salts and sodium EDTA. In addition, parenteral solutions can contain preservatives, such as benzalkonium chloride, methyl or propyl-paraben, and chlorobutanol.

Suitable pharmaceutical carriers are described in *Remington's Pharmaceutical Sciences*, A. Osol. a standard reference text in this field.

Useful pharmaceutical dosage forms for administration of the compounds of this invention can be illustrated as follows:

CAPSULES

A large number of unit capsules are prepared by filling standard two-piece hard gelatin capsules each with 50 milligrams of powdered active ingredient, 175 milligrams of lactose, 24 milligrams of talc, and 6 milligrams of magnesium stearate.

SOFT GELATIN CAPSULES

A mixture of active ingredient in soybean oil is prepared and injected by means of a positive displacement pump into gelatin to form soft gelatin capsules containing 50 milligrams of the active ingredient. The capsules are washed in petroleum ether and dried.

TABLETS

A large number of tablets are prepared by conventional procedures so that the dosage unit is 50 milligrams of active ingredient, 6 milligrams of magnesium stearate, 70 milligrams of microcrystalline cellulose, 11 milligrams of cornstarch and 225 milligrams of lactose. Appropriate coatings may be applied to increase palatability or delay absorption.

INJECTABLE

A parenteral composition suitable for administration by injection is prepared by stirring 1.5% by weight of active ingredient in 10% by volume propylene glycol and water. The solution is sterilized by commonly used techniques.

SUSPENSION

An aqueous suspension is prepared for oral administration so that each 5 milliliters contain 25 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

NASAL SPRAY

An aqueous solution is prepared such that each 1 milliliter contains 10 milligrams of active ingredient, 1.8 milligrams methylparaben, 0.2 milligrams propylparaben and 10 milligrams methylcellulose. The solution is dispensed into 1 milliliter vials.

LUNG INHALER

A homogeneous mixture of the active ingredient in polysorbate 80 is prepared such that the final concentration of the active ingredient will be 10 milligrams per container and the final concentration of polysorbate 80 in the container will be 1% by weight. The mixture is dispensed into each can, the valves are crimped onto the can and the required amount of dichlorotetrafluoroethane is added under pressure.

TOPICAL FORMULATION

An ointment for topical administration may be prepared by adding the active ingredient to a mixture of 48% by weight white petrolatum, 10% liquid petrolatum, 8% glycerol monostearate, 3% isopropyl myristate and 20% lanolin at 70° C. After thorough mixing, a warm solution of methyl and propyl parabens in water containing sodium acetone bisulfite is added such that the final concentration of each paraben is 0.15%, of water is 8%, and of sodium acetone bisulfite is 0.5%. The mixture is stirred until it has reached room temperature.

PHOSPHOLIPASE $A_2$ INHIBITION TEST SYSTEM

The compounds of this invention have been shown to inhibit phospholipase $A_2$ in an in vitro test system using the porcine pancreatic $PLA_2$ enzyme and an assay modified from Hirata et al. (*Proc. Natl. Acad. Sci* (USA), 77, 2533, 1980). The reaction was run in a total volume of 0.1 ml with the enzyme at a final concentration of 19 units/ml (0.025 μg protein/ml) which gave approximately 5000–8000 dpm (disintegration per minute) of activity in a buffer containing 25 mM Tris (trihydroxymethyl aminoethane), 25 mM glycylglycine, 25 mM $CaCl_2$ and 0.75 mM EDTA (tetra sodium salt), pH 8.5. The drug was added to the enzyme solution, incubated for 2 minutes, and the substrate, [arachidonyl-1-$^{14}$C] L-α-1-palmitoyl-2-arachidonyl phosphatidylcholine, at a final concentration of 7 μM (40,000 dpm), was then added to begin the reaction which proceeded for five minutes at 37° C. The reaction was stopped by freezing in a dry ice-ethanol slurry and the arachidonic acid products were separated from the unreacted substrate using silica gel columns.

All reactions were run in duplicate. Inhibitors were dissolved in 0.2M Tris-Cl (trihydroxymethyl aminoethane hydrochloride), pH 8.5 or dissolved in DMSO and then diluted with Tris-Cl buffer (maximum DMSO concentration, 7%). The IC50 value was determined by inspection of a semilog plot of percent inhibition versus final inhibitor concentration.

The enzyme phospholipase $A_2$ ($PLA_2$), catalyzes the release of fatty acids from the 2-position of phospholipids, particularly phosphatidyl choline. Arachidonic acid (AA) is most frequently found at the 2-position of phospholipids. Once it is released by the action of $PLA_2$, AA can be oxygenated by cyclooxygenases and lipoxygenases to the potent inflammatory mediators, prostaglandins and leukotrienes, respectively. Inhibition of $PLA_2$ will block the generation of these local inflammatory mediators, thereby reducing inflammation. Since AA is the substrate for both cyclooxygenases and lipoxygenases, inhibition of $PLA_2$ will reduce the levels of both prostaglandins and leukotrienes. Many current anti-inflammatory drugs, e.g., salicylates, inhibit cyclooxygenases but not lipoxygenases, so that only prostaglandin levels are reduced.

TPA INFLAMMATION INHIBITION TEST

The compounds of Formula (I) have been shown to be efficacious in murine models of skin inflammatory diseases. One such model is the inflammation induced by tetradecanoyl phorbol acetate (TPA), modified from the method of Kuehl et al., *Nature*, 1977, 265, 170; and Van Arman, *Clin. Pharmacol. Ther.*, 1974, 16, 900. The TPA model mimics many of the inflammatory changes which occur in human skin diseases such as psoriasis, since elevated levels of inflammatory arachidonic acid metabolites are found and an influx of polymorphonuclear leukocytes is observed. The test procedure used to evaluate the compounds of Formula (I) is as follows: the test compound (100 mg/ear) is applied to both ears of mice in an appropriate vehicle, such as acetone, and then the inflammatory stimulus (TPA) is applied to the right ear. Four hours later, the edema is measured by removing standard size discs from the ears using a biopsy punch. A control group of animals receives TPA in vehicle applied to the right ear, and vehicle alone to the left ear. The weights of the ear discs are determined, and the suppression of swelling observed in animals treated with the test compound is determined. Results obtained in this model for selected compounds of Formula (I) are shown in Table III.

TABLE III

| Example | % Inhibition of Control Swelling |
| --- | --- |
| 1 | 89 |
| 5 | 46 |
| 7 | 22 |
| 8 | 50 |
| 10 | 24 |
| 11 | 45 |
| 21 | 68 |
| 22 | 26 |
| 26 | 52 |
| 27 | 51 |
| 28 | 51 |
| 30 | 34 |
| 34 | 22 |
| 36 | 48 |
| 38 | 30 |
| 39 | 50 |
| 40 | 29 |
| 42 | 22 |
| 44 | 25 |
| 56 | 64 |
| 57 | 60 |
| 61 | 25 |

"Consisting essentially of" in the present disclosure is intended to have its customary meaning; namely, that all specified materials and conditions are very important in practicing the invention but that unspecified materials and conditions are not excluded so long as they do not prevent the benefits of the invention from being realized.

What is claimed is:

1. A substituted benzylamine phospholipase $A_2$ inhibitor of the formula:

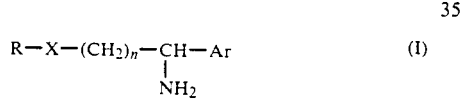

or a pharmaceutically acceptable salt thereof, wherein Ar is

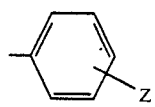

and Z is H, F, Cl, Br, $-OR^1$, or $-S(O)_mR^1$, where $R^1$ is H, $-CH_3$, or $-C_2H_5$, and m is 0, 1, or 2; n is 1 to 5;
X is NH; and
R is $C_7$-$C_{25}$ alkyl, or a mono- or polycyclic benzoid aromatic system of the formula:

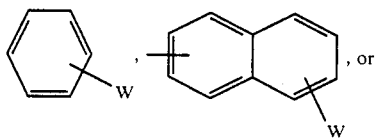

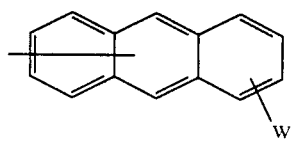

where W is $C_1$-$C_{20}$ alkyl, F, Cl, Br, $-OR^2$, $-S(O)_qR^2$, $-C(CF_3)_2OH$, or phenyl, and $R_2$ is $-CH_3$ or $-C_2H_5$, and q is 0, 1, or 2; or R is benzhydryl, alkaryl or substituted alkaryl of 7 to 25 carbon atoms, where the substitution is on the aromatic moiety, and is F, Cl, Br, $-OR^3$, $-S(O)_rR^3$, or $C_1$-$C_{10}$ alkyl, where $R^3$ is $-CH_3$ or $-C_2H_5$, and r is 0, 1, or 2;

provided that:
a) when Z is H, X is NH, and n is 2, then R cannot be benzhydryl;
b) when X is NH, then R cannot be phenyl or benzyl.

2. A substituted benzylamine phospholipase $A_2$ inhibitor of claim 1, wherein
Z is H, F, Cl, Br, $-OCH_3$, or $-S(O)_mCH_3$, where m is 0, 1, or 2;
n is 1, 2, or 3; and
X is NH.

3. A substituted benzylamine phospholipase $A_2$ inhibitor of claim 2, wherein
Ar is

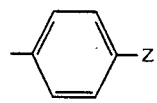

wherein Z is H, F, Cl, $-OCH_3$, or $-SCH_3$;
n is 2 or 3; and
R is $C_{10}$-$C_{12}$ alkyl, or

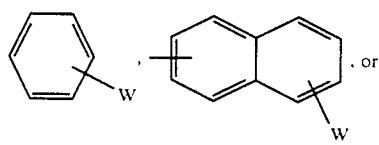

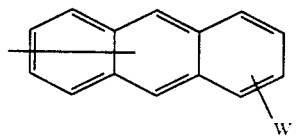

where W is $C_1$-$C_{12}$ alkyl,
or R is alkaryl or substituted alkaryl of 7 to 25 carbon atoms, where the substitution is on the aryl moiety, and is $-OCH_3$, $-SCH_3$, F, Cl, or $C_1$-$C_{10}$ alkyl.

4. The compound of claim 3 which is α-(2-[1,4a-Dimethyl-7-(2-propyl)-1,2,3,4,4a,9,10,10a-octahydro-1-phenanthrenylmethylamino]ethyl)-4-fluorobenzenemethanamine Dihydrochloride.

5. The compound of claim 3 which is 4-Fluoro-α-(2-[2-(2-naphthalenyl)ethylamino]-ethyl)benzenemethanamine Dihydrochloride.

6. The compound of claim 3 which is 4-Fluoro-α-(4-[1,4a-dimethyl-7-(2-propyl)-1,2,3,4,4a,9,10,10a-octahydro-1-phenanthrenylmethylamino]propyl)benzenemethanamine Dihydrochloride.

7. The compound of claim 3 which is 4-Fluoro-α-(3-[(2-naphthalenyl)ethylamino]propyl)benzenemethanamine dihydrochloride.

8. The compound of claim 3 which is 4-Methylthio-α-(2-[2-(2-naphthalenyl)ethylamino]-ethyl)benzenemethanamine Dihydrochloride.

9. The compound of claim 3 which is 4-Fluoro-α-(2-decylaminoethyl)benzenemethanamine Dihydrochloride.

10. The compound of claim 3 which is 4-Methoxy-α-(2-[2-(2-naphthalenyl)ethylamino]-ethyl)benzenemethanamine Dihydrochloride.

11. The compound of claim 3 which is 2-(2-[1,4a-Dimethyl-7-(2-propyl)-1,2,3,4,4a,9,10,10a-octahydro-1-phenanthrenylmethylamino]ethyl)benzenemethanamine Dihydrochloride.

12. The compound of claim 3 which is α-(2-[1,4a-Dimethyl-7-(2-propyl)-1,2,3,4,4a,9,10,10a-octahydro-1-phenanthrenylmethylamino]ethyl)-4-methoxybenzenemethanamine Dihydrochloride.

13. The compound of claim 3 which is α-(2-[1,4a-Dimethyl-7-(2-propyl)-1,2,3,4,4a,9,10,10a-octahydro-1-phenanthrenylmethylamino]ethyl)-4-methylthio-benzenemethanamine Dihydrochloride.

14. A pharmaceutical composition, consisting essentially of a substituted benzylamine phospholipase $A_2$ inhibitor of claim 1 in an amount sufficient to provide anti-inflammatory and/or anti-allergic effects in a mammal suffering from a phospholipase $A_2$-mediated condition, and a pharmaceutically acceptable carrier.

15. A pharmaceutical composition, consisting essentially of a substituted benzylamine phospholipase $A_2$ inhibitor of claim 2 in an amount sufficient to provide anti-inflammatory and/or anti-allergic effects in a mammal suffering from a phospholipase $A_2$-mediated condition, and a pharmaceutically acceptable carrier.

16. A pharmaceutical composition, consisting essentially of a substituted benzylamine phospholipase $A_2$ inhibitor of claim 3 in an amount sufficient to provide anti-inflammatory and/or anti-allergic effects in a mammal suffering from a phospholipase $A_2$-mediated condition, and a pharmaceutically acceptable carrier.

17. A pharmaceutical composition according to claim 14 wherein the substituted benzylamine phospholipase $A_2$ inhibitor is α-(2-[1,4a-Dimethyl-7-(2-propyl)-1,2,3,4,4a,9,10,10a-octahydro-1-phenanthrenylmethylamino]ethyl)-4-fluoro-benzenemethanamine Dihydrochloride.

18. A pharmaceutical composition according to claim 14 wherein the substituted benzylamine phospholipase $A_2$ inhibitor is 4-Fluoro-α-(2-[2-(2-naphthalenyl)ethylamino]-ethyl)benzenemethanamine Dihydrochloride.

19. A pharmaceutical composition according to claim 14 wherein the substituted benzylamine phospholipase $A_2$ inhibitor is 4-Fluoro-α-(4-[1,4a-dimethyl-7-(2-propyl)-1,2,3,4,4a,9,10,10a-octahydro-1-phenanthrenylmethylamino]propyl)benzenemethanamine Dihydrochloride.

20. A pharmaceutical composition according to claim 14 wherein the substituted benzylamine phospholipase $A_2$ inhibitor is 4-Fluoro-α-(3-[(2-naphthalenyl)ethylamino]propyl)benzenemethanamine Dihydrochloride.

21. A pharmaceutical composition according to claim 14 wherein the substituted benzylamine phospholipase $A_2$ inhibitor is 4-Methylthio-α-(2-[2-(2-naphthalenyl)ethylamino]ethyl)benzenemethanamine Dihydrochloride.

22. A pharmaceutical composition according to claim 14 wherein the substituted benzylamine phospholipase $A_2$ inhibitor is 4-Fluoro-α-(2-decylaminoethyl)benzenemethanamine Dihydrochloride.

23. A pharmaceutical composition according to claim 14 wherein the substituted benzylamine phospholipase $A_2$ inhibitor is 4-Methoxy-α-(2-[2-(2-naphthalenyl)ethylamino]ethyl)benzenemethanamine Dihydrochloride.

24. A pharmaceutical composition according to claim 14 wherein the substituted benzylamine phospholipase $A_2$ inhibitor is 2-(2-[1,4a-Dimethyl-7-(2-propyl)-1,2,3,4,4a,9,10,10a-octahydro-1-phenanthrenylmethylamino]ethyl)benzenemethanamine Dihydrochloride.

25. A pharmaceutical composition according to claim 14 wherein the substituted benzylamine phospholipase $A_2$ inhibitor is α-(2-[1,4a-Dimethyl-7-(2-propyl)-1,2,3,4,4a,9,10,10a-octahydro-1-phenanthrenylmethylamino]ethyl)-4-methoxy-benzenemethanamine Dihydrochloride.

26. A pharmaceutical composition according to claim 14 wherein the substituted benzylamine phospholipase $A_2$ inhibitor is α-(2-[1,4a-Dimethyl-7-(2-propyl)-1,2,3,4,4a,9,10,10a-octahydro-1-phenanthrenylmethylamino]ethyl)-4-methylthio-benzenemethanamine Dihydrochloride.

27. A pharmaceutical composition of claim 14 which is formulated for topical administration.

28. A pharmaceutical composition of claim 15 which is formulated for topical administration.

29. A pharmaceutical composition of claim 16 which is formulated for topical administration.

30. A pharmaceutical composition of claim 27 wherein the substituted benzylamine phospholipase $A_2$ inhibitor is α-(2-[1,4a-Dimethyl-7-(2-propyl)-1,2,3,4,4a,9,10,10a-octahydro-1-phenanthrenylmethylamino]ethyl)-4-fluoro-benzenemethanamine, or a pharmaceutically acceptable salt thereof.

31. A pharmaceutical composition of claim 27 wherein the substituted benzylamine phospholipase $A_2$ inhibitor is 4-Fluoro-α-(4-[1,4a-dimethyl-7-(2-propyl)-1,2,3,4,4a,9,10,10a-octahydro-1-phenanthrenylmethylamino]propyl)benzenemethanamine, or a pharmaceutically acceptable salt thereof.

32. A pharmaceutical composition of claim 27 wherein the substituted benzylamine phospholipase $A_2$ inhibitor is 2-(2-[1,4a-Dimethyl-7-(2-propyl)-1,2,3,4,4a,9,10,10a-octahydro-1-phenanthrenylmethylamino]ethyl)benzenemethanamine, or a pharmaceutically acceptable salt thereof.

33. A pharmaceutical composition of claim 27 wherein the substituted benzylamine phospholipase $A_2$ inhibitor is α-(2-[1,4a-Dimethyl-7-(2-propyl)-1,2,3,4,4a,9,10,10a-octahydro-1-phenanthrenylmethylamino]ethyl)-4-methoxy-benzenemethanamine, or a pharmaceutically acceptable salt thereof.

34. A pharmaceutical composition of claim 27 wherein the substituted benzylamine phospholipase $A_2$ inhibitor is 4-fluoro-α-[2-(octylamino)ethyl]benzenemethanamine, or a pharmaceutically acceptable salt thereof.

35. A pharmaceutical composition of claim 27 wherein the substituted benzylamine phospholipase $A_2$ inhibitor is 4-Fluoro-α-[2-heptylamino)ethyl]benzenemethanamine, or a pharmaceutically acceptable salt thereof.

36. A pharmaceutical composition of claim 27 wherein the substituted benzylamine phospholipase $A_2$ inhibitor is 4-Fluoro-α-[2-undecylamino)ethyl]benzenemethanamine, or a pharmaceutically acceptable salt thereof.

37. A pharmaceutical composition of claim 27 wherein the substituted benzylamine phospholipase $A_2$ inhibitor is 4-Fluoro-α-[2-(hexylamino)ethyl]benzenemethanamine, or a pharmaceutically acceptable salt thereof.

38. A pharmaceutical composition of claim 27 wherein the substituted benzylamine phospholipase $A_2$ inhibitor is 4-Fluoro-α-(2-[1-(3-adamantyl)ethylamino]ethyl)-benzenemethanamine, or a pharmaceutically acceptable salt thereof.

39. A method of treating inflammatory and/or allergic conditions mediated by phospholipase $A_2$ in a mammal, comprising administering to the mammal a therapeutically effective amount of a substituted benzylamine phospholipase $A_2$ inhibitor of claim 1.

40. A method of treating inflammatory and/or allergic conditions mediated by phospholipase $A_2$ in a mammal, comprising administering to the mammal a therapeutically effective amount of a substituted benzylamine phospholipase $A_2$ inhibitor of claim 2.

41. A method of treating inflammatory and/or allergic conditions mediated by phospholipase $A_2$ in a mammal, comprising administering to the mammal a therapeutically effective amount of a substituted benzylamine phospholipase $A_2$ inhibitor of claim 3.

42. A method of treating inflammatory and/or allergic conditions mediated by phospholipase $A_2$ in a mammal, comprising administering to the mammal a therapeutically effective amount of the substituted benzylamine phospholipase $A_2$ inhibitor of claim 4.

43. A method of treating inflammatory and/or allergic conditions mediated by phospholipase $A_2$ in a mammal, comprising administering to the mammal a therapeutically effective amount of the substituted benzylamine phospholipase $A_2$ inhibitor of claim 5.

44. A method of treating inflammatory and/or allergic conditions mediated by phospholipase $A_2$ in a mammal, comprising administering to the mammal a therapeutically effective amount of the substituted benzylamine phospholipase $A_2$ inhibitor of claim 6.

45. A method of treating inflammatory and/or allergic conditions mediated by phospholipase $A_2$ in a mammal, comprising administering to the mammal a therapeutically effective amount of the substituted benzylamine phospholipase $A_2$ inhibitor of claim 7.

46. A method of treating inflammatory and/or allergic conditions mediated by phospholipase $A_2$ in a mammal, comprising administering to the mammal a therapeutically effective amount of the substituted benzylamine phospholipase $A_2$ inhibitor of claim 8.

47. A method of treating inflammatory and/or allergic conditions mediated by phospholipase $A_2$ in a mammal, comprising administering to the mammal a therapeutically effective amount of the substituted benzylamine phospholipase $A_2$ inhibitor of claim 9.

48. A method of treating inflammatory and/or allergic conditions mediated by phospholipase $A_2$ in a mammal, comprising administering to the mammal a therapeutically effective amount of the substituted benzylamine phospholipase $A_2$ inhibitor of claim 10.

49. A method of treating inflammatory and/or allergic conditions mediated by phospholipase $A_2$ in a mammal, comprising administering to the mammal a therapeutically effective amount of the substituted benzylamine phospholipase $A_2$ inhibitor of claim 11.

50. A method of treating inflammatory and/or allergic conditions mediated by phospholipase $A_2$ in a mammal, comprising administering to the mammal a therapeutically effective amount of the substituted benzylamine phospholipase $A_2$ inhibitor of claim 12.

51. A method of treating inflammatory and/or allergic conditions mediated by phospholipase $A_2$ in a mammal, comprising administering to the mammal a therapeutically effective amount of the substituted benzylamine phospholipase $A_2$ inhibitor of claim 13.

* * * * *